(12) United States Patent
Thatte et al.

(10) Patent No.: US 8,945,823 B2
(45) Date of Patent: *Feb. 3, 2015

(54) COMPOSITIONS AND METHODS FOR TISSUE PRESERVATION

(75) Inventors: Hemant Thatte, Medfield, MA (US); Patrick Treanor, Dedham, MA (US); Shukri F. Khuri, Needham, MA (US); Randa Khuri, legal representative, Needham, MA (US); Laki Rousou, New York, NY (US)

(73) Assignee: The United States of America as Represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/552,255

(22) Filed: Jul. 18, 2012
(Under 37 CFR 1.47)

(65) Prior Publication Data

US 2012/0282591 A1 Nov. 8, 2012

Related U.S. Application Data

(63) Continuation of application No. 13/488,749, filed on Jun. 5, 2012, which is a continuation of application No. 12/527,119, filed as application No. PCT/US2008/002170 on Feb. 19, 2008, now Pat. No. 8,211,628.

(60) Provisional application No. 60/901,844, filed on Feb. 17, 2007, provisional application No. 60/902,587, filed on Feb. 20, 2007, provisional application No. 60/966,511, filed on Aug. 27, 2007.

(51) Int. Cl.
*A01N 1/00* (2006.01)
*A01N 1/02* (2006.01)

(52) U.S. Cl.
CPC ............... *A01N 1/02* (2013.01); *A01N 1/0226* (2013.01)
USPC ............................................. 435/1.1; 435/1.2

(58) Field of Classification Search
CPC ............................. A01N 1/02; A01N 1/0226
See application file for complete search history.

(56) References Cited

U.S. PATENT DOCUMENTS

| | | | |
|---|---|---|---|
| 4,256,834 A | 3/1981 | Zuk et al. |
| 4,415,556 A | 11/1983 | Bretschneider |
| 4,675,314 A | 6/1987 | Strumia |
| 4,798,824 A | 1/1989 | Belzer et al. |
| 4,879,283 A | 11/1989 | Belzer et al. |
| 5,075,210 A | 12/1991 | Wikman-Coffelt |
| 5,130,230 A | 7/1992 | Segall et al. |
| 5,200,398 A | 4/1993 | Strasberg et al. |
| 5,243,044 A | 9/1993 | Dandliker et al. |
| 5,279,937 A | 1/1994 | Rowe |
| 5,554,497 A | 9/1996 | Raymond |
| 5,714,515 A | 2/1998 | Bunger |
| 5,945,272 A | 8/1999 | Segall et al. |
| 6,028,107 A | 2/2000 | Waugh |
| 6,046,046 A | 4/2000 | Hassanein |
| 6,492,103 B1 | 12/2002 | Taylor |
| 6,521,248 B1 | 2/2003 | Holloway et al. |
| 6,524,785 B1 | 2/2003 | Cozzone et al. |
| 6,528,540 B2 | 3/2003 | Liu et al. |
| 6,569,615 B1 | 5/2003 | Thatte et al. |
| 6,680,305 B1 | 1/2004 | Segall et al. |
| 6,994,954 B2 | 2/2006 | Taylor |
| 7,198,254 B2 | 4/2007 | Holloway et al. |
| 2002/0132220 A1 | 9/2002 | Berens et al. |
| 2003/0124503 A1 | 7/2003 | Olivencia-Yurvati et al. |
| 2004/0009894 A1 | 1/2004 | Hobai et al. |
| 2004/0018245 A1 | 1/2004 | Steen |
| 2004/0038192 A1 | 2/2004 | Brasile |
| 2005/0136391 A1 | 6/2005 | Steinhardt |
| 2005/0147958 A1 | 7/2005 | Hassanein et al. |
| 2005/0202394 A1 | 9/2005 | Dobson |
| 2006/0154357 A1 | 7/2006 | Hassanein et al. |
| 2006/0154359 A1 | 7/2006 | Hassanein et al. |
| 2007/0098694 A1 | 5/2007 | Khuri et al. |
| 2007/0254862 A1 | 11/2007 | Antel et al. |
| 2012/0282591 A1 | 11/2012 | Thatte et al. |

FOREIGN PATENT DOCUMENTS

| | | |
|---|---|---|
| CN | 1791341 A | 6/2006 |
| EP | 0199117 A2 | 10/1986 |
| EP | 1000541 A1 | 5/2000 |
| WO | WO-9211773 A1 | 7/1992 |
| WO | WO-0101774 A1 | 1/2001 |
| WO | WO-0130754 A2 | 5/2001 |

(Continued)

OTHER PUBLICATIONS

Gibco BRL Catalog, p. 119, Hanks' Balanced Salt Solutions (1992).*
Boehm et al. "Adenosine Cardioplegia: Reducing Reperfusion Injury of the Ischaemic Myocardium?" *J. Mol. Cell. Cardio.* 22.S5(1990). (Abstract #P13).
Ikeda et al. "Cardioprotective Effects of Citrulline in Ischemia/Reperfusion Injury Via a Non-Nitric Oxide-Mediated Mechanism." *Method, Find. Exp. Clin. Pharmacol.* 22.7(2000):563-571.
Lango et al. "Influence of L-carnitine and its Derivatives on Myocardial Metabolism and Function in Ischemic Heart Disease and During Cardiopulmonary Bypass." *Cardiovasc. Res.* 51.1(2001):21-29.
Michel. "Evaluation of a New Preservative Solution for Cardiac Graft During Hypothermia." *J. Heart Lung Transplant.* 19.11(2000):1089-1097.

(Continued)

*Primary Examiner* — Sandra Saucier
(74) *Attorney, Agent, or Firm* — Mintz Levin Cohn Ferris Glovsky and Popeo, P.C.; Ingrid A. Beattie

(57) ABSTRACT

Methods and compositions for resuscitating, storing, and preserving functional integrity of organs and tissues. Metabolic function is maintained by sustaining ATP levels, mitochondrial function, cardiomyocyte contractility, prevention of acidosis, inhibition of induction of apoptosis, maintaining ionontrophy and lusiotrophy by regulating calcium, sodium, potassium and chloride ions.

9 Claims, 16 Drawing Sheets

(56) References Cited

FOREIGN PATENT DOCUMENTS

| WO | WO-0205870 A2 | 1/2002 |
|---|---|---|
| WO | WO-02102149 A1 | 12/2002 |
| WO | WO-2004084807 A2 | 10/2004 |
| WO | WO-2005103080 A2 | 11/2005 |
| WO | WO-2006065920 A1 | 6/2006 |
| WO | WO-2006133273 A2 | 12/2006 |
| WO | WO-2008016937 A2 | 2/2008 |

OTHER PUBLICATIONS

Puetz et al. "Effects of L-Carnitine-Hydrochloride in the Cold Ischemic Preservation of Fatty Liver Grafts," *Transplant. Proc.* 33(2001):2523-2524.
Southard et al. "Important Components of the UW Solution1,2." *Transplant.* 49.2(1990):251-257.
Boku et al. "A Comparative Study of Cardiac Preservation with Celsior or University of Wisconsin Solution with or without Prior Administration of Cardioplegia." *J. Heart Lung Transplant.* 25(2006):219-225.
Ferrera et al. "Comparison of Different Techniques of Hypothermic Pig Heart Preservation." *Ann. Thorac. Surg.* 57(1994):1233-1239.
Hearse et al. "Creatine Phosphate and Protection Against Reperfusion-Induced Arrhymias in the Rat Heart." *Eur. J. Pharmacol.* 131.1(1986):21-30.
Igarashi et al. "Calcium-Independent Activation of Endothelial Nitric Oxide Synthase by Ceramide." *PNAS.* 96.22(1999):12583-12588.
Maurer et al. "Comparison of UW and Collins Solution for Preservation of the Rat Heart." *Transplant. Pro.* 22.2(1990):548-550.
Nakatsubo et al. "Direct Evidence of Nitric Oxide Production From Bovine Aortic Rndothelial Cells Using New Fluorescence Indicators: Diaminofluoresceins." *FEBS Lett.* 427.2(1998):263-266.
Oshima et al. "Long-Term Heart Preservation Using a New Portable Hypothermic Perfusion Apparatus." *J. Heart Lung Transplant.* 18.9(1999):852-861.
Swanson et al. "Improved Heart Preservation with UW Preservation Solution." *J. Heart Transplant.* 7(1988):456-467.
Thatte et al. "The Coronary Artery Bypass Conduit: I. Intraoperative Endothelial Injury and Its Implication on Graft Patency." *Ann. Thorac. Surg.* 72(2001):S2245-S2252.
Abe. "Role of Histidine-Related Compounds as Intracellular Proton Buffering Constituents in Vertebrate Muscle." *Biochem. (Mosc).* 65(2000):757-765.
Bae et al. "Effects of Lacidipine on Vascular Responses in Patients with Coronary Artery Disease." *Int. J. Cardiol.* 101.3(2005):377-383.
Baptiste et al. "Effects of Minocycline and Tetracycline on Retinal Ganglion Cell Survival after Axotomy." *Neurosci.* 134(2005):575-582.
Crespi. "Dihydropyridines, Nitric Oxide and Vascular Protection." *Curr. Vasc. Pharmacol.* 3.2(2005):195-205.

Di et al. "Rapid Glucocorticoid-Mediated Endocannabinoid Release and Opposing Regulation of Glutamate and GABA Inputs to Hypothalamic Magnocellular Neurons." *Endocrin.* 145.10(2005):4292-4301.
Fernandez-Gomez et al. "Involvement of Mitochondrial Potential and Calcium Buffering Capacity in Minocycline Cytoprotective Actions." *Neurosci.* 133.4(2005):959-967.
Hoffman et al. "Effect of Creatine and β-Alanine Supplementation on Performance and Endocrine Responses in Strength /Power Athtletes." *Int. J. Sport Nutr. Ecxer. Metab.* 16(2006):430-446.
Hohmann et al. "An Endocannabinoid Mechanism for Stress-Induced Analgesia." *Nature.* 435(2005:1108-1112.
Kocak-Toker et al. "Peroxynitrite Induced Decrease in $Na^+$, $K^+$-ATPase Activity is Restored by Taurine." *World J. Gastroenterol.* 11.23(2005):3554-3557.
Kurabayashi et al. "2-Arachidonoylglycerol Increases in Ischemia-Reperfusion Injury of the Rat Liver." *J. Invest. Surg.* 18.1(2005):25-31.
Loriette et al. "Dietary Casein Levels and Taurine Supplementation. Effects on Cysteine Dioxygenase and Cysteine Sulfinate Decarboxylase Activities and Taurine Concentration in Brain, Liver and Kidney of the Rat." *Nutr. Metab.* 23.6(1979):467-475.
Molchanova et al. "Mechanisms of Enhanced Taurine Release Under $Ca^{2+}$ Depletion." *Neurochem. Int.* 47(2005):343-349.
Oriyanhan et al. "Taurine Prevents Myocardial Ischemia-Reperfusion-Induced Oxidative Stress and Apoptosis in Prolonged Hypothermic Rat Heart Preservation." *Heart Vessels.* 20(2005):278-285.
Panikashvili et al. "$CB_1$ Cannabinoid Receptors are Involved in Neuroprotection via NF-κB Inhibition." *J. Cereb. Blood Flow Metab.* 25.4(2005):477-484.
Tian et al. "The Conformation, Location, and Dynamic Properties of the Endocannabinoid Ligand Anandamide in a Membrane Bilayer." *J. Biol. Chem.* 280.33(2005):29788-29795.
Wang et al. "Minocycline Inhibits LPS-Induced Retinal Microglia Activation." *Neurochem. Int.* 47(2005):152-158.
Zaliunas et al. "Effects of Amlodipine and Lacidipine on Heart Rate Variability in Hypertensive Patients with Stable Angina Pectoris and Isolated Left Ventricular Diastolic Dysfunction." *Int. J. Cardiol.* 101.3(2005):347-353.
Zoeller et al. "Effects of Creatine and Beta-Alanine on Ventilatory and Lactate Thresholds in Men." *Amino Acids.* 33(2006):505-510.
't Hart et al. "New Solutions in Organ Preservation." *Transpl. Rev.* 16.3(2002):131-141.
Demertzis et al. "University of Wisconsin Versus St. Thomas' Hospital Solution for Human Donor Heart Preservation." *Ann. Thorac. Surg.* 55.5(1993):1131-1137.
Ingemansson et al. "Importance of Calcium in Long-Term Preservation of the Vasculature." *Ann. Thorac. Sug.* 61.4(1996):1158-1162.
Reddy et al. "Liver Transplantation From Non-Heart-Beating Donors: Current Status and Future Prospects." *Liver Transpl.* 10.10(2004):1223-1232.

* cited by examiner

COMPOSITIONS AND METHODS FOR TISSUE PRESERVATION

RELATED U.S. APPLICATIONS

This application is a continuation of U.S. application Ser. No. 13/488,749, filed Jun. 5, 2012, which is a continuation of U.S. application Ser. No. 12/527,119, filed Aug. 13, 2009, which claims priority to International Application No. PCT/US2008/002170, filed Feb. 19, 2008, and which claims priority to U.S. Provisional Application No. 60/901,844 filed Feb. 17, 2007, U.S. Provisional Application No. 60/902,587, filed Feb. 20, 2007, and U.S. Provisional Application No. 60/966,511, filed Aug. 27, 2007, each of which is incorporated herein by reference in its entirety.

FIELD OF THE INVENTION

The present invention relates to tissue preservation.

BACKGROUND OF THE INVENTION

The major obstacles in cardiac transplantation are the limited availability of donor hearts and the poor quality of donor hearts due to deterioration during storage. Using current practices and preservation solutions, the limit of preservation time is 4-6 hours, and in the United States, all cardiac allografts are presently obtained from brain-dead, beating heart donors maintained on life support systems. Moreover, current practices result in a significant incidence of accelerated vasculopathy in transplanted hearts. As such, there is a pressing need for long-term storage solutions that preserve the structural and physiological integrity of donor hearts.

SUMMARY OF THE INVENTION

The invention provides a solution for preserving a human or human-compatible harvested organ in need of preservation or resuscitation during a preservation or evaluation period prior to implantation, including transplantation or reimplantation. The solution of the invention also allows the organ to be transported to alternate geographic locations during the preservation period. The invention provides improved compositions, methods, and devices for organ storage, which preserve the functional integrity of the organ as well as restore the function to a non-functioning or deteriorated organ. Increasing the use of non-beating heart (NBH) donors and storage of donor hearts for a longer period of time would increase the size of the donor pool substantially and allow transport of donor hearts over longer distances to increase availability to recipients. Transplantation of hearts with intact, functioning coronary endothelium as a result of storage in the improved solution minimizes vasculopathy that occurs after cardiac transplantation using current technology.

The invention provides for compositions for preserving or resuscitating a biological tissue. The composition contains a physiological salt solution and at least one, at least two, at least three, at least four, or at least five of the following compositions: a substrate for the production of adenosine tri phosphate (ATP), a substrate for the consumption of ammonia, a reagent that buffers intracellular acidity, a reagent that quenches reactive oxygen species, and/or a reagent that balances tissue edema/dehydration.

In one aspect, the composition contains a physiological salt solution and a substrate for the production of ATP. Optionally, the substrate for the production of ATP is phosphocreatine, creatine ethyl ester, dicreatine malate, creatine gluconate, fructose, sucrose, ribose, hexose or pentose. Alternatively, the substrate for the production of ATP is creatine orotate, creatine monohydrate, adenosine, or dextrose/glucose.

The composition for preserving or resuscitating a biological tissue contains a physiological salt solution and a compound for the consumption of ammonia. Optionally, the compound for the consumption of ammonia is ornithine or carbomyl phosphate. Alternatively, the compound for the consumption of ammonia is L-citrulline malate.

In another aspect, the composition for preserving or resuscitating a biological tissue contains a physiological salt solution and a reagent that buffers intracellular acidity. In one aspect, the reagent that buffers intracellular acidity is Histidine, Glutamine, Tryptophan, Lysine, or Taurine. Alternatively, the reagent that buffers intracellular acidity is sodium bicarbonate, THAM, or L-carnosine.

Optionally, the composition for preserving or resuscitating a biological tissue contains a physiological salt and a reagent that quenches reactive oxygen species. In one aspect, the reagent that quenches reactive oxygen species is dithiothreitol (DTT), beta-Mercaptoethanol, Acetylcysteine, Alpha lipoic acid, Taurine, Reserveratrol, Lutein, Selenium, Methionine, or Tocopherols/Vitamin E.

In yet another aspect, the composition for preserving or resuscitating a biological tissue contains a physiological salt and a reagent that balances tissue water content (edema/dehydration). Reagents that balance tissue water content include Mannitol, urea, glycerine, isosorbide, or raffinose pentahydrate. Optionally, the reagent that balances tissue water content is the penta fraction of raffinose pentahydrate.

The solution is used to resuscitate a living donor heart, a temporally stored living donor heart for transplantation, as well as cadaveric donor heart and permits extended temporal storage of living, stored, or cadaveric organs such as the heart. Cardiomyocyte function in living donor and cadaveric hearts are preserved as well as endothelial function in coronary vasculature and chambers of the living donor and the cadaveric heart. The solution also mediates reversal of metabolic and degenerative changes and inhibition of cell death and progression to cell viability in the hearts (and other organs) when the organ is contacted with and stored in the solution of the invention shortly after death. Metabolic function is maintained by sustaining ATP levels, mitochondrial function, cardiomyocyte contractility, prevention of acidosis, inhibition of induction of apoptosis. Ionontrophy and lusiotrophy are maintained by regulating calcium, sodium, potassium and chloride ions. Buffering capacity of the solution prevent acidosis. The solution preserves calcium mobilization, nitric oxide generation in the organ as well as maintains both endothelium-dependent and independent vasomotor function in the coronary vasculature. Dehydration and subsequent over-hydration (edema) is prevented upon reperfusion by manipulating ionic concentrations and aquaporin channels, and ischemia-reperfusion injury is prevented. The solution and storage system is a self-sustaining regenerative system for production of substrates for ATP and nitric oxide.

The compositions prevent ischemia-reperfusion injury. This function is mediated by ascorbic acid and glutathione, carnitine (by preventing accumulation of long chain acyl-CoA that leads to generation of free radicals-ischemi-reperfusion injury), carnosine and alpha lipoic acid which are free radical, (hydroxyl radical, singlet oxygen, peroxyl radical and superoxide) scavenger. The composition contains calcium chloride, potassium chloride, potassium phosphate, magnesium sulfate, sodium bicarbonate, D-glucose, adenosine, glutathione, insulin, and a reagent to prevent dehydration and/or edema of an organ and/or tissue. The solution also contains other salts such as magnesium chloride, sodium chloride, and/or sodium phosphate dibasic.

Dehydration of the heart (during storage) and over-hydration or edema after reperfusion is controlled by manipulating sodium (less) and potassium ions (more) (i.e., osmolarity). The solution is slightly hypotonic and hyposmolar, hence driving the water into the heart during storage and balancing out during reperfusion. The increase in external KCl concentration counterbalances the K current (close to Nerst potential) and prevents potassium from moving out along with water (shell of hydration of K ion). Dehydration/edema is also controlled by manipulating the aquaporin channels via the ionic currents. Also, external K may delay/decrease the movement of Ca ions into the cell, thus preventing dehydration via Ca activated K channel. For example, the solution contains 125 mM sodium and 7 mM potassium. In one aspect, the composition contains calcium chloride, potassium chloride, potassium phosphate, magnesium sulfate, sodium bicarbonate, D-glucose, adenosine, glutathione, insulin, and a substrate for the production of ATP. For example, the substrate for the production of ATP is creatine orotate, creatine monohydrate, adenosine, or dextrose/glucose. Dichloroacetate increases ATP production by inhibiting the kinase enzyme that phosphorylates PDH enzyme making it inactive. Dichloroacetate induces ATP synthesis by facilitating the TCA cycle.

In the citrulline malate-arginine cycle, malate (cleaved from citrulline) enters the TCA cycle to generate more ATP. Also, citrulline malate is converted to arginine and fumarate; fumarate enters the TCA cycle to facilitate more ATP production. Both malate and fumarate in TCA cycle leads to more ATP production.

The composition contains calcium chloride, potassium chloride, potassium phosphate, magnesium sulfate, sodium bicarbonate, D-glucose, adenosine, glutathione, insulin, and a reagent that buffers acidity. A reagent that buffers intracellular acidity is creatine orotate via facilitated synthesis of carnosine. Creatine monohydrate buffers acidity by increasing energy production and decreased lactate accumulaton. Acidity is also buffered by sodium bicarbonate, Tris-hydroxymethyl aminomethane (THAM), and L-carnosine (intracellular acidity). Dichloroacetate controls acidity by lowering lactate levels in the preserved organ, and thus the solution. L-carnitine facilitates a decrease in myocardial lactate production, hence reducing acidity.

The composition contains calcium chloride, potassium chloride, potassium phosphate, magnesium sulfate, sodium bicarbonate, D-glucose, adenosine, glutathione, insulin, and a substrate for the consumption of ammonia. For example, the substrate for the consumption of ammonia is L-citrulline malate. Ammonia combines with carbamoyl phosphate to form citrulline malate, which forms a substrate for nitric oxide and ATP.

The composition contains calcium chloride, potassium chloride, potassium phosphate, magnesium sulfate, sodium bicarbonate, D-glucose, adenosine, glutathione, insulin, a reagent to prevent dehydration and/or edema of an organ and/or tissue, a substrate for the production of ATP, a reagent that buffers acidity, and a substrate for the consumption of ammonia. Preferably, the composition includes the following compounds and concentrations:

about 0.147 g/L calcium chloride (1 mM)
  about 0.52 g/L potassium chloride (7 mM)
  about 0.06 g/L potassium phosphate (monobasic) (0.44 mM)
  about 0.11 g/L magnesium chloride (hexahydrate) (0.50 mM)
  about 0.125 g/L magnesium sulfate (heptahydrate) (0.50 mM)
  about 7.30 g/L sodium chloride (125 mM)
  about 0.35 g/L sodium bicarbonate (4.2 mM)
  about 0.05 g/L sodium phosphate (dibasic; heptahydrate) (0.19 mM)
  about 1.98 g/L dextrose/D-glucose (11 mM)
  about 0.27 g/L adenosine (1 mM)
  about 0.46 g/L glutathione (reduced; 1.5 mM)
  about 0.18 g/L ascorbic acid (1 mM)
  about 0.21 g/L L-arginine (1 mM)
  about 0.27 g/L creatine orotate (0.5 mM)
  about 0.30 g/L creatine monohydrate (2 mM)
  about 0.15 g/L L-citrulline malate (1 mM)
  about 0.08 g/L dichloroacetate (0.5 mM)
  about 2.3 g/L-carnosine (10 mM)
  about 2.0 g/L-carnitine (10 mM)
  about 0.021 g/L Alpha-Lipoic acid (0.1 mM)
  about 0.50 ml/L insulin (10 mg/ml)
  THAM (Tris-Hydroxymethyl Aminomethane; 100 mM stock @12.1 gm/L) to adjust
  pH (about 1 L distilled water).

The ingredients are mixed together to form a solution. Insulin is optionally added after the other ingredients are mixed. For example, insulin is added minutes, e.g., 0.5, 1, 2, 5, minutes to hours, e.g., 0.5, 1, 2, 3, 4, or 5 hours prior to immersing an organ in the solution.

A preferred composition includes amounts of the compounds in the following ranges to achieve a desired ratio of compositions:

0.1-0.5 g/L calcium chloride
  0.25-0.75 g/L potassium chloride (7 mM)
  0.01-0.5 g/L potassium phosphate (monobasic)
  0.01-0.5 g/L magnesium chloride (hexahydrate)
  0.01-0.5 g/L magnesium sulfate (heptahydrate)
  5.0-10.0 g/L sodium chloride (125 mM)
  0.01-0.5 g/L sodium bicarbonate
  0.01-0.5 g/L sodium phosphate (dibasic; heptahydrate)
  1.0-5.0 g/L D-dextrose/glucose (11 mM)
  0.01-0.5 g/L adenosine (1 mM)
  0.01-0.75 g/L glutathione (reduced; 1.5 mM)
  0.01-0.5 g/L ascorbic acid (1 mM)
  0.01-0.5 g/L L-arginine (1 mM)
  0.01-0.5 g/L creatine orotate (0.5 mM)
  0.01-0.5 g/L creatine monohydrate (2 mM)
  0.01-0.5 g/L L-citrulline malate (1 mM)
  0.01-0.5 g/L dichloroacetate (0.5 mM)
  0.23-2.3 g/L-carnosine (1-10 mM)
  0.20-2.0 g/L-carnitine (1-10 mM)
  0.0021-0.21 g/L Alpha-Lipoic acid (0.01-1.0 mM)
  0.25-0.75 ml/L insulin (10 mg/ml)
  THAM to adjust pH (0.01-3.0 L distilled water).

For example, the solution contains:

about 0.14 g/L calcium chloride
  about 0.52 g/L potassium chloride (7 mM)
  about 0.06 g/L potassium phosphate (monobasic)
  about 0.10 g/L magnesium chloride (hexahydrate)
  about 0.10 g/L magnesium sulfate (heptahydrate)
  about 7.31 g/L sodium chloride (125 mM)
  about 0.35 g/L sodium bicarbonate
  about 0.05 g/L sodium phosphate (dibasic; heptahydrate)
  about 1.98 g/L dextrose/D-glucose (11 mM)
  about 0.27 g/L adenosine (1 mM)
  about 0.46 g/L glutathione (reduced; 1.5 mM)
  about 0.18 g/L ascorbic acid (1 mM)
  about 0.21 g/L L-arginine (1 mM)
  about 0.27 g/L creatine orotate (0.5 mM)

about 0.30 g/L creatine monohydrate (2 mM)
about 0.15 g/L L-citrulline malate (1 mM)
about 0.08 g/L dichloroacetate (0.5 mM)
about 2.3 g/L-carnosine (10 mM)
about 2.0 g/L-carnitine (10 mM)
about 0.021 g/LAlpha-Lipoic acid (0.1 mM)
about 0.50 ml/L insulin (10 mg/ml)
THAM to adjust pH (about 1 L distilled water).

The solutions described above are used to maintain the physiological integrity of an organ. The organ or tissue, which is preferably isolated from a human body or the body of an animal, is contacted for a duration of at least 1 hour. Alternatively, the organ or tissue is perfused in situ, i.e., prior to being removed from the body. For example, the organ or tissue is contacted in situ in a cadaver or in a living patient. The organ or tissue is contacted with the solution from a period of about 1-5 hours, e.g., 4 hours up to several days, e.g., 1, 2, 5, 8, days or more.

A variety of different organs and tissue types are favorably stored and resuscitated using the solutions. For example, the organ or tissue is a heart. Other suitable tissues/organs include kidney, liver, stomach, spleen, pancreas, lung, brain, eye, intestines, bladder, skin or dermal tissue, blood vessels such as veins or arteries, heart valves, sperm, and oocyte(s).

The method of maintaining or restoring the physiological integrity of an organ or tissue is carried out by contacting the organ or tissue with the solution(s) described above for a duration of time such that esterase activity is in the range of >150 arbitrary fluorescence photon units, intracellular NO concentration is in the range of >1 nM, and mitochondrial membrane potential ratio of the cells of the organ is >1.00. The solution preserves intact cardiac myocyte contractile proteins (myosin heavy chain (HC), myosin light chain (LC), acitinin, actin, troponinc C); eNOS, caveolin, and vWF, e.g., as assessed with Western and Immunoblots, whereas storage of tissues/organs such as heart in previous solutions led to degradation of such proteins such as myosin heavy chain thereby compromising the integrity and function of the transplanted organ. Absence or fragmentation of these compostions indicate deterioration of the organ. Clinical parameters include Left Ventricular End Diastolic Pressure (LVEDP) 0-30 mm Hg, BP 100-140/60-100, pH>6.8. The solution also inhibits stenosis, plaques, clot formation due to damaged endothelium, as well formation of an atheroma (arterial sclerosis), which is a significant problem in transplant cases.

Also within the invention is a method of evaluating the physiological integrity of an organ or tissue. The organ or tissue is contacted with solution(s) described above (or another solution) and a level of concentration or activity of one or more of the following parameters is detected or evaluated. Biological indices to be evaluated include esterase, nitric oxide, or cellular membrane potential. Esterase activity is in the range of >150 arbitrary (fluorescence photon) units, intracellular NO concentration is in the range of >1 nM, and mitochondrial membrane potential of the cells of said organ is in the range of >1.00 (ratio of polarized versus depolarized, where >1 indicates that the mitochondrial membrane is polarized and the tissue is healthy. The foregoing values indicate that the organ or tissue, e.g., a heart, is suitable for transplantation into a recipient living mammal.

The compositions for making the storage/resuscitation solution are optionally packaged in a kit with the ingredients/amounts listed below or multiples thereof, i.e., scaled up to make 2, 3, 5, 10, 20 times the amount of solution. An exemplary kit contains
0.1-0.5 g/L calcium chloride
0.25-0.75 g/L potassium chloride (7 mM)
0.01-0.5 g/L potassium phosphate (monobasic)
0.01-0.5 g/L magnesium chloride (hexahydrate)
0.01-0.5 g/L magnesium sulfate (heptahydrate)
5.0-10.0 g/L sodium chloride (125 mM)
0.01-0.5 g/L sodium bicarbonate
0.01-0.5 g/L sodium phosphate (dibasic; heptahydrate)
1.0-5.0 g/L D-glucose (11 mM)
0.01-0.5 g/L adenosine (1 mM)
0.01-0.75 g/L glutathione (reduced; 1.5 mM)
0.01-0.5 g/L ascorbic acid (1 mM)
0.01-0.5 g/L L-arginine (1 mM)
0.01-0.5 g/L creatine orotate (0.5 mM)
0.01-0.5 g/L creatine monohydrate (2 mM)
0.01-0.5 g/L L-citrulline malate (1 mM)
0.01-0.5 g/L dichloroacetate (0.5 mM)
0.23-2.3 g/L-carnosine (1-10 mM)
0.20-2.0 g/L-carnitine (1-10 mM)
0.0021-0.21 g/LAlpha-Lipoic acid (0.01-1.0 mM)
0.25-0.75 ml/L insulin (10 mg/ml)
THAM to adjust pH These ingredients packaged together with instructions for use and are mixed in 0.01-2.0 L of distilled water. As is described above, insulin is optionally added shortly before use, i.e., shortly before an organ is added to the solution. The kit is packaged or sold without the sterile water component. For example, the kit contains
about 0.14 g/L calcium chloride
about 0.52 g/L potassium chloride (7 mM)
about 0.06 g/L potassium phosphate (monobasic)
about 0.10 g/L magnesium chloride (hexahydrate)
about 0.10 g/L magnesium sulfate (heptahydrate)
about 7.31 g/L sodium chloride (125 mM)
about 0.35 g/L sodium bicarbonate
about 0.05 g/L sodium phosphate (dibasic; heptahydrate)
about 1.98 g/L dextrose/D-glucose (11 mM)
about 0.27 g/L adenosine (1 mM)
about 0.46 g/L glutathione (reduced; 1.5 mM)
about 0.18 g/L ascorbic acid (1 mM)
about 0.21 g/L L-arginine (1 mM)
about 0.27 g/L creatine orotate (0.5 mM)
about 0.30 g/L creatine monohydrate (2 mM)
about 0.15 g/L L-citrulline malate (1 mM)
about 0.08 g/L dichloroacetate (0.5 mM)
about 2.3 g/L-carnosine (10 mM)
about 2.0 g/L-carnitine (10 mM)
about 0.021 g/LAlpha-Lipoic acid (0.1 mM)
about 0.50 ml/L insulin (10 mg/ml)
THAM to adjust pH Optionally, the solution is nano-sized to increase the efficiency of traversing the cellular membrane. Nano-sizing refers to the reduction of the particle size to the sub-micron range, with the final particle size typically being 1-10 ηm. The reduction of particle size leads to a significant increase in the efficiency of the solution in traversing the cellular membrane. In one aspect, the efficiency is increased such that at least 20%, at least 25%, at least 50%, at least 75%, or at least 100% of the solution traverses the cellular membrane.

The invention provides for nano-sizing for the solution of the invention prior to use in the methods described herein. Alternatively, the invention provides for nano-sizing the water prior to adding the other compounds/reagents of the solution. In yet another aspect, the invention provides for nano-sizing the water and nano-sizing each compound/reagent of the solution separately prior to mixing in solution.

In one aspect, the composition comprises water packets or water clusters in a nanometer range of size. Optionally, the water packets or water clusters are 1-10 ηm, 1-25 ηm, 25-50 ηm, 50-75 ηm, 75-100 ηm, 100-200 ηm, 200-500 ηm, or 500-999 ηm.

The invention also provides methods of measuring the pH of an excised heart comprising contacting the excised heart with the solution of the invention, and determining the pH of the excised heart, wherein a pH between 6.8 and 7.0 indicates the heart is suitable for transplantation.

The invention also provides methods of measuring the pH of the solution of the invention comprising contacting an excised heart with the solution of the invention, and determining the pH of the solution of the invention, wherein a pH between 6.8 and 7.0 indicates said heart is suitable for transplantation.

In addition to solutions and methods of storing/preserving organs and tissues, the invention includes a perfusion device. Elements of the device include a chamber assembly, a perfusion circuit including a first conduit for providing the solution to the organ, and a temperature control unit. The device includes an immobilized phosphoenolpyruvate (PEP) carboxykinase and lactate dehydrogenase (LDH) columns to make it a self sustaining system. For example, the solution coming out of the heart chamber may contain some lactic acid, which is then continuously converted to pyruvate by the LDH as the solution is pumped back into the chamber. Pyruvate then enters the TCA cycle for continuous generation of ATP. Similarly, oxaloacetate that is formed in the TCA cycle is converted to Phosphoenol pyruvate by PEP carboxykinase. PEP is converted to pyruvate producing ATP. Also, pyruvate enters the TCA cycle to generate more ATP. Thus, the device permits the cycle to continue regenerating substrates. Energy metabolism is sustained in the system until all the glucose and/or fatty acids are consumed only upon prolonged storage, e.g., greater than about 2 weeks or 10 days. For example, the device is suitable for vascular tissue such as heart and blood vessels, as well as kidney, liver, stomach, spleen, pancreas, lung, brain, eye, intestines, and bladder.

A system for maintenance or resuscitation of a mammalian organ includes a container for keeping the organ in contact with the composition or solution described above, a delivery means for delivering the composition to at least one vascular vessel of the organ, a removal means for transport of the composition away from the organ, a temperature control means, an oxygenation means, a filtering means, and a flow control means. The delivery means, removal means, temperature means, oxygenation means, filtering means, and flow control means provide or restore a physiological acceptable mammalian environment. A self-sustaining system includes the following elements: continuous production of nitric oxide, continuous generation of ATP, buffering of acidosis and hydrogen ions, and quenching of ammonia. The elements are preferably interconnected.

Other features and advantages of the invention will be apparent from the following description of the preferred embodiments thereof, and from the claims. All references cited herein are hereby incorporated by reference.

DETAILED DESCRIPTION OF THE INVENTION

Figure 1:
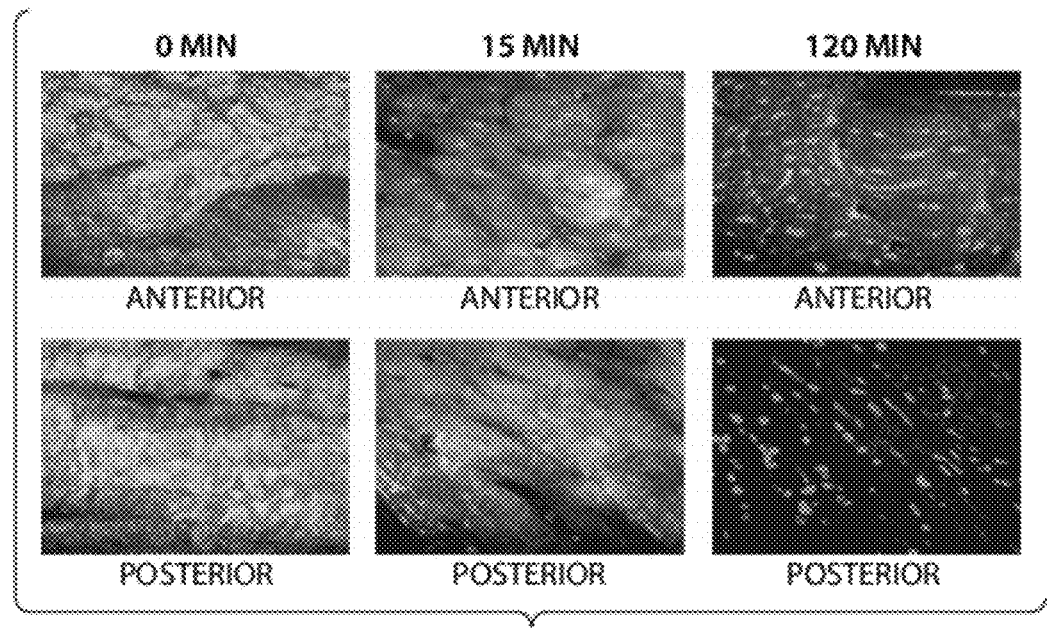
FIG. 1 is a series of photomicrographs depicting the esterase activity (green) and cellular necrosis (red) of ventricular cardiomyocytes in the anterior and posterior left ventricular (LV) wall at 0 minutes, 15 minutes and 120 minutes post-harvest.

The present invention provides a novel storage solution for donor hearts taking into account various biochemical processes that occur during storage of an organ for transplantation. The solution permits a substantially longer preservation period, the use of non-beating heart (NBH) donors, and improved clinical outcomes for those receiving cardiac transplants. The solution includes compositions the address various damaging processes (listed below) that occur during storage of an organ.

Techniques for the preservation of the donor heart for transplantation have changed very little despite 30 years of extensive research in the field. In cardiac transplantation, major obstacles are the limited availability and poor quality of donor hearts after some amount of storage time. Using current practices and preservation solutions, the limit of preservation time is 4-6 hours (Ferrera Ret al., 1994 *Ann Thorac Surg*, 57:1233-1239; Oshima K et al., 1999 *J of Heart and Lung Trans*, 18(9): 852-861), and in the United States, all cardiac allografts are presently obtained from brain-dead, beating heart donors maintained on life support systems. As a result of this severely limited organ pool and time restraints on preservation, 10%-40% of all cardiac transplant candidates die awaiting a new organ. In addition, currently there is a significant incidence of accelerated vasculopathy in transplanted hearts presumably due, in part, to the poor quality of donor hearts after storage.

The ability to store donor hearts for a longer period of time would increase the size of the donor pool and allow for transport of donor hearts longer distances to suitable recipients. Moreover, superior preservation might allow for the use of non-beating heart donors (NBHD) and further increase the donor pool. Finally, improvement of the condition of donor hearts after storage would improve the clinical results for the recipient.

The preservation of a harvested donor human heart prior to transplant entails protection of endothelial cells, cardiac myocyte function, and mechano-contractile coupling, and is related to the long-term survival of a transplanted heart. Despite advances in science and technology of prolonging organ viability and storage, few changes have been made in the clinical practice of donor heart preservation during the past 20 years. The currently available preservation protocols use hypothermic arrest and simple storage using a variety of crystalloid-based cardioplegic and preservation solutions, and are limited in terms of the length of storage of 4-6 hours. In addition, these techniques invariably subject donor hearts to periods of global ischemia that may result in functional and metabolic stunning leading to ischemia-reperfusion injury. In addition, the two major limitations of successful long term cardiac transplantation today are the lack of enough donor hearts to meet the demand of the large number of patients who potentially could benefit from transplantation, and the relatively high rate of long-term transplanted heart failures, which are primarily due to accelerated atherosclerotic disease.

Surgical techniques for harvesting and transplantation of the human heart are very well established. What happens to the explanted heart during storage generally dictates the successful outcome of the transplant. Therefore, there is a pressing need for storage solutions and conditions. The invention provides storage solutions, methods and devices that maintain the structural and functional integrity of explanted donor hearts and thus prolongs ex-vivo storage prior to surgical re-implantation. Application of this newly developed technology should enable the resuscitation of an arrested heart within 30 minutes of the arrest. As such, patients dying in the emergency room due to non-cardiac trauma can become potential heart donors for transplantation.

This invention provides a system for preserving harvested human heart (or other organs) in need of preservation or resuscitation during preservation and evaluation period prior to implantation and/or transplantation. This system allows for organs to be preserved at normothermic temperatures in viable state (and be transported to alternate geographic locations for transplantation if required), thus potentially increasing the extremely limited availability of these much-needed organs. In order to preserve the heart in a viable state, the invention considers both the anaerobic and aerobic modes of metabolism, the requirements for endogenous vasodialators and an energy source. The preservation solution described herein maintains the viability of the organ for an extended period, e.g., about 1 hour, about 2 hours, about 3 hours, about 4 hours, about 8 hours, about 10 hours, about 15 hours, about 20 hours, or about 1 day. The solution of the invention provides nutrients suitable for cardiac myocyte and endothelial cell energy metabolism. In another aspect, the solutions provide protective ingredients that can help the tissues/cells resist the damaging effects of prolonged storage. Moreover, the solutions provide protection against desiccation and rehydration edema upon transplantation.

The invention also provides a perfusion system that allows for circulation of the solution not only through the coronary vasculature, but also all the compartments of the static heart. This ensures that the nutrient rich solution bathes the whole organ inside and outside.

The invention also provides a method to gently prime the heart with nutrients and intermediate metabolites prior to transplantation. Such priming of the heart physiologically converts the static heart into a restored sinus rhythm without detrimental contractures and ischemia-reperfusion injury.

Thus, the compositions, methods, systems/devices and media of the present invention can preserve, resuscitate and maintain the donor heart in either the static or beating state during the time of preservation to insure homogenous distribution of the preservation medium. Maintaining the heart in the beating state further serves to sustain normal metabolic, contractile, and endothelial functions beyond the current 4-6 hour window of hypothermic arrest and storage for donor hearts.

The invention provides a novel storage solution for donor hearts taking into account various biochemical processes that occur during storage of an organ for transplantation. The solution of the invention will allow a substantially longer preservation period, the use of NBH donors, and improved clinical outcomes for those receiving cardiac transplants.

Following are some potentially damaging processes that occur during storage of an organ and how they are addressed by the solution of the invention. Reactive oxygen species are generated during storage; however, ascorbic acid and reduced glutathione (i.e. reducing agents) present in the solution consume oxygen free radicals during storage. Hydrogen ion production during storage can lead to acidosis; however, the solution contains agents with buffering activity. ATP is diminished during storage; however, the solution contains substrates for the production of ATP and maintenance of metabolic mechanisms in the heart. Ammonia is produced as a result of the breakdown of amino acids during storage; however, the solution contains substrates for the consumption of ammonia and production of substrate for anaerobic/aerobic metabolism. Storage can also result in dehydration/edema of the organ; however, the ionic composition of the solution is manipulated in order to maintain normal water content in the cell to prevent edema in the reperfused myocyte. This also provides an ideal environment for myocyte contraction.

Figure 23:
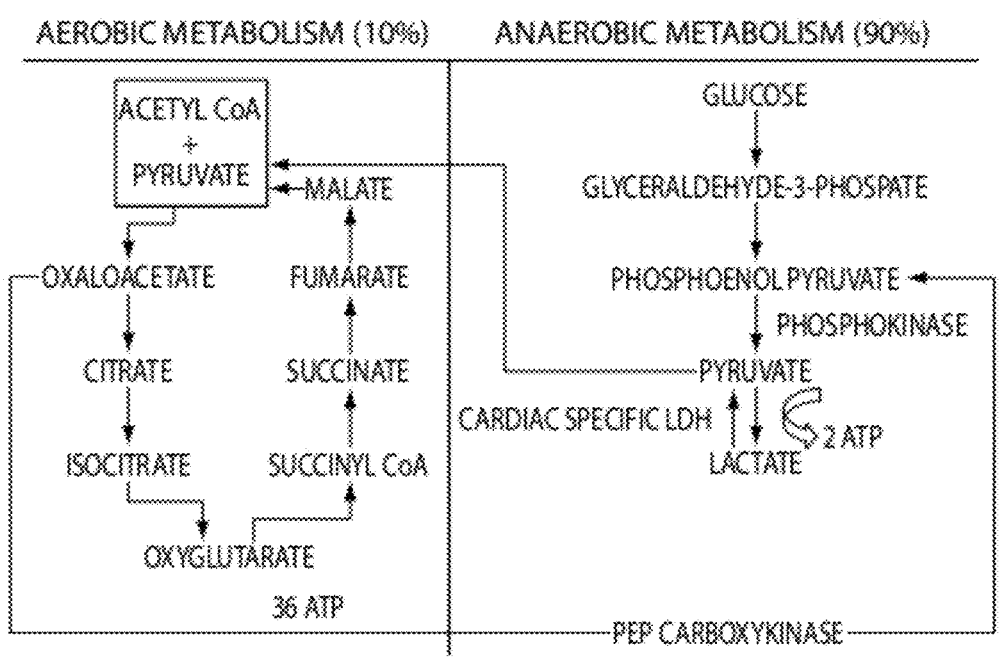
FIG. 23 is a diagram showing the energy metabolism in the heart during storage.
Figure 24:
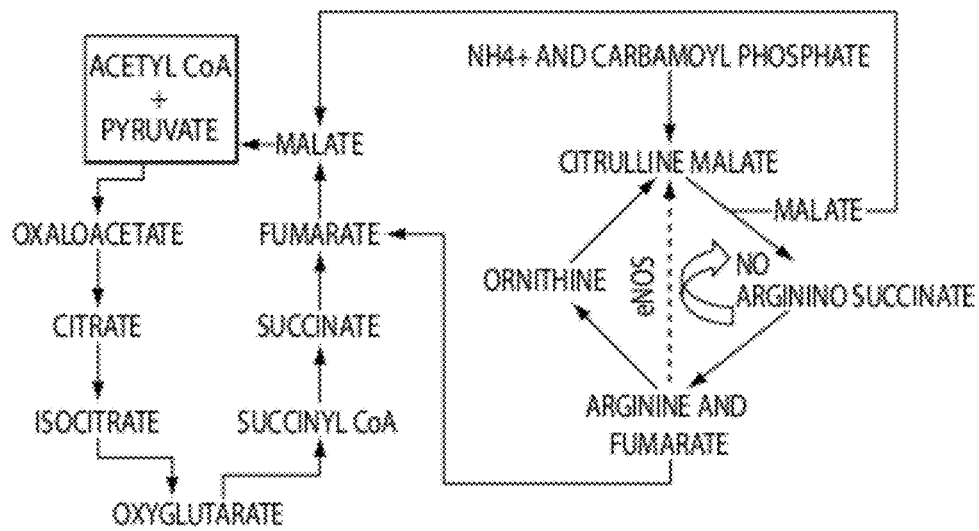
FIG. 24 is a diagram illustrating the ammonia production in the heart during storage.
Figure 25:
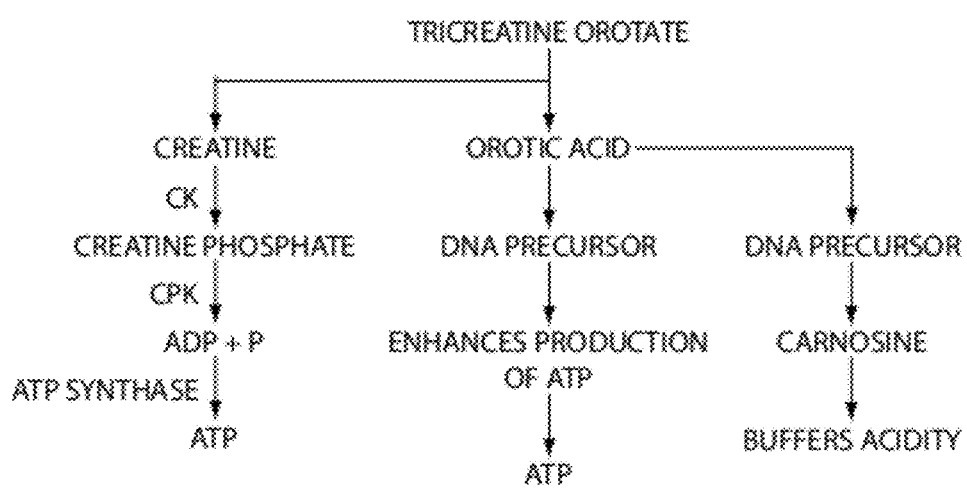
FIG. 25 is a diagram demonstrating the role of creatine in the production of ATP and the maintenance of metabolic mechanisms in the heart during storage.

FIGS. 23-25 illustrate some metabolic pathways in the heart during storage and how these processes are addressed by the solutions of the invention. FIG. 23 illustrates energy metabolism pathways in the heart during storage, while FIG. 24 depicts pathways pertaining to ammonia production in the heart. FIG. 25 depicts energy metabolism in the heart relating to ATP stores and production of hydrogen ions.

Myocardial Dehydration During Storage

Figure 29:
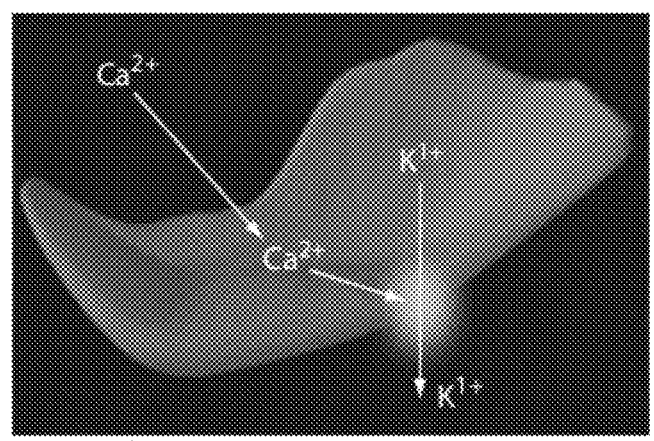
FIG. 29 is a drawing illustrating a Gardos channel.
Figure 30:
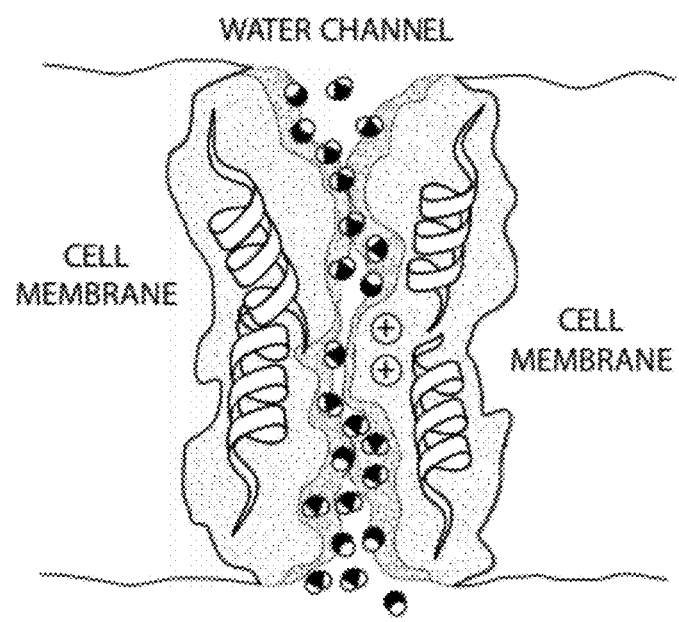
FIG. 30 is a drawing of an aquaporin (water channel).

A significant problem in organ storage is dehydration. For example, in heart tissue, myocardial dehydration occurs via the following metabolic processes. A decrease in ATP leads to an increase in $Na^+$ in the cell, secondary to $Na^+$ leak and decrease in Na—K ATPase activity. The Na—Ca exchanger reverses causing $Ca^+$ to build up in the cell. Subsequently, a further increase in $Ca^+$ results in $Ca^+$-induced $Ca^+$ release from the sarcoplasmic reticulum (SR). $Ca^+$ also induces the GARDOS Channel, which leads to the loss of $K^+$ and water (FIG. 29). Aquaporins are a route for water out of the cell, and upon reperfusion, back into the cell (FIG. 30.)

In order to counteract the above-mentioned sequence of events, the solution contains a relatively low $Na^+$ concentration (about 125 mM) and a slightly higher $K^+$ concentration (7 mM). By preventing the dehydration of the myocardium, the solutions of the invention prevent the rapid uptake of water into the cells once perfusion is reestablished.

Prior to the invention described herein, none of the currently available organ storage solutions had adequately addressed the potential role of activated hemichannels and/or aquaporins in induction of edema and ionic imbalance in the stored organs, especially the heart. Connexin 43 containing hemichannels, that are also the components of gap junctions, and aquaporins (AQP1) have been demonstrated in cardiomyocytes and the endothelial cells in the heart. Activation of these channels may play an important role in development of ionic disproportion, edema, and stiffness of the organs during storage. Increased cell volume (edema) and stiffness can lead to the failure of the organ upon transplant, or may require significant pharmacological intervention to reverse this trend before the organ can function. Problems associated with these channels being activated is addressed by the invention to improve viable preservation of stored organs.

Optimizing the solution of the invention would prevent activation of hemichannels, thus avoiding edema, ionic imbalance and energy depletion during organ storage. These constituents provide a favorable environment and cellular support during ex-vivo storage. As shown in the Examples below, the protection of structure and function of cardiomyocytes and the endothelium in BHD and NBHD hearts, stored over a prolonged period in the solution of the invention, supports this hypothesis.

A decrease in physiological concentration of external calcium (<1-1.3 mM), a reduction in glutathione (altered redox potential), energy state (<ATP), phosphorylation, or in activation of MAP kinase, or any increase in reactive oxygen species and osmolarity leads to opening of hemichannels. All of these parameters, which are encountered by the heart or organ during storage, can operate independently of one another in activating the hemichannels. Opening of hemichannels, because of nonselectivity, allows free flow of external $Na^+$, $Cl^-$, and $Ca^{2+}$ into, and $K^+$ out of the cytoplasm. Due to the build up of excess intracellular negative charges (negatively charged macromolecules), the increase in internal $Cl^-$ concentration would require water uptake via AQP1 and/or hemichannels to maintain isosmotic condition. Subsequent closing of the channels would establish a higher steady state cell volume. However, to counterbalance the increased volume and to avoid rupture, the cell compensates by rearranging the cytoskeleton leading to cell stiffness. Increased cell volume (edema) and stiffness leads to the failure of the organ upon transplant, or may require significant pharmacological intervention to reverse this trend before the organ can function. Activation of hemichannels leads to water and ion accumulation and edema in the heart during storage. Components of the solution of the invention, including physiological concentration of calcium, will prevent any of the above-mentioned detrimental changes from taking place in the stored organs.

Optionally, the solution is nano-sized to increase the efficiency of the solution traversing the cellular membrane by any method known in the art, including the method described in U.S. Pat. Nos. 6,521,248 and 7,198,254, which are incorporated herein by reference in their entireties. Nano-sizing refers to the reduction of the particle size to the sub-micron range, with the final particle size typically being 1-10 ηm. The reduction of particle size leads to a significant increase in the efficiency of the solution in traversing the cellular membrane. In one aspect, the efficiency is increased such that at least 20%, at least 25%, at least 50%, at least 75%, or at least 100% of the solution traverses the cellular membrane.

The invention provides for nano-sizing for the solution of the invention prior to use in the methods described herein. Alternatively, the invention provides for nano-sizing the water prior to adding the other compounds/reagents of the solution. In yet another aspect, the invention provides for nano-sizing the water and nano-sizing each compound/reagent of the solution separately prior to mixing in solution.

In one aspect, the composition comprises water packets or water clusters in a nanometer range of size. Optionally, the water packets or water clusters are 1-10 ηm, 1-25 ηm, 25-50 ηm, 50-75 ηm, 75-100 ηm, 100-200 ηm, 200-500 ηm, or 500-999 ηm.

Increasing storage time significantly, improving condition of donor hearts/organs after storage, and allowing for the use of NBHD will have a profound impact on the current landscape of transplant surgery. Immediate impact could be achieved if the solution is used in place of current preservation solutions.

Assessment of myocardial and endothelial structure and function at the cellular level indicates that solution can accomplish each one of those goals. Structure and function of the myocardium is significantly improved after storage in the solution of the invention, referred to as "Lazarus", if compared to Celsior (a commonly used storage solution for cardiac transplants) when the conditions are exactly the same. Furthermore, these parameters are still preserved after one hour of death (NBHD) and 10 days or two weeks of storage.

Example 1

General Methods

Experiments were performed to compare Lazarus to Celsior (a presently used storage solution in cardiac transplantation) with respect to their effects on the myocardium and coronary endothelium as assessed using various microscopic and biochemical analyses. Comparisons were made using beating heart and NBHD models.

The Lazarus solution contained the following:

| | |
|---|---|
| Calcium chloride | 0.14 gm/L |
| Potassium chloride (7 mM) | 0.52 gm/L |
| Potassium phosphate (monobasic) | 0.06 gm/L |
| Magnesium chloride (hexahydrate) | 0.10 gm/L |
| Magnesium sulfate (heptahydrate) | 0.10 gm/L |
| Sodium chloride (125 mM) | 7.31 gm/L |
| Sodium bicarbonate | 0.35 gm/L |
| Sodium phosphate (dibasic; hepatahydrate) | 0.05 gm/L |
| D-Glucose (11 mM) | 1.98 gm/L |
| Adenosine (1 mM) | 0.27 gm/L |
| Glutathione (reduced; 1.5 mM) | 0.46 gm/L |
| Ascorbic acid (1.0 mM) | 0.18 gm/L |
| L-Arginine (1 mM) | 0.21 gm/L |
| Creatine orotate (0.5 mM) | 0.27 gm/L |
| Creatine monohydrate (2 mM) | 0.30 gm/L |
| L-Citrulline (1 mM) | 0.15 gm/L |
| Dichloroacetate (0.5 mM) | 0.08 gm/L |
| Insulin (10 mg/ml) | 0.50 ml/L |
| Distilled water | 1.00 L |

Animal Protocol

Figure 28:
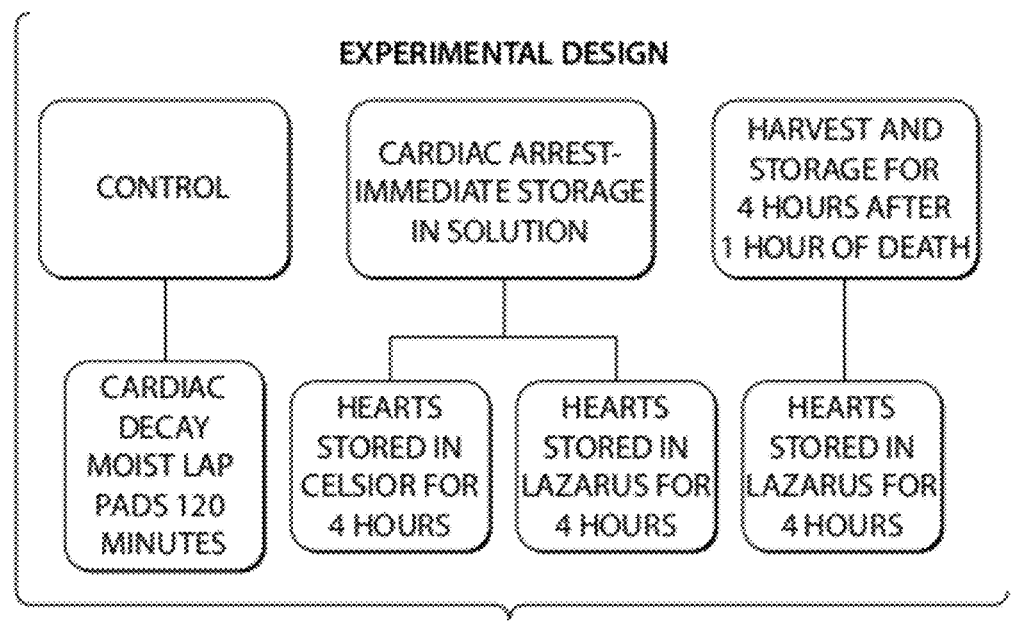
FIG. 28 is a diagram depicting an experimental design.

All animals in the study received humane care in compliance with the "Guide for the Care and Use of Laboratory Animals." Studies to evaluate organ storage solutions were carried out using the following animal protocol. The study included three experimental groups and one control group with three pigs (sus scrofa) in each group. In the control group, the heart was harvested and kept moist with saline soaked laparotomy pads to mimic cardiac decay. Biopsies and biochemical analyses were done at regular intervals representing cardiac decay without intervention. In the experimental groups, there were 9 pigs (45-50 kg); three pigs in each group. Data was collected using multi-photon microscopy and other biochemical analyses (Western and Immunoblots) to evaluate the structure and function of the myocardium and coronary endothelium after storage in solution for 4 hours. The experimental design is illustrated in FIG. 28.

For each animal, weight was recorded on the morning of the experiment. Each was given an intramuscular injection (IM) of Telazol 4-6 mg/kg and Xylazine 2 mg/kg IM then intubated and connected to a respirator on 100% oxygen. Intravenous access was obtained through an ear vein with an 18 gauge needle. Anesthesia was maintained with 1-2% Isolfurane during the course of the experiment and EKG leads were placed for continuous monitoring. The right femoral artery was exposed and cannulated using an 18 gauge catheter for continuous blood pressure monitoring on the Power Lab.

A sternotomy was performed and the pericardium was opened and elevated using 2-0 silk sutures to the skin. Next, Kuri myocardial pH probes were inserted using a probe inside the right atrium as a reference probe. The posterior left ventricular (LV) wall electrode was placed first and secured with a 3-0 chromic suture. The anterior LV wall electrode was then secured in the same manner. Five minutes was allowed for the probes to equilibrate and myocardial pH and temperature were monitored using the pH monitor throughout of the rest of the experiment. In experimental groups 1 and 2, 300 mg/kg of heparin was given through the arterial line. After waiting 5-10 minutes for the heparin to take effect, a 12-gauge cannula was placed in the ascending aorta for infusion of cardioplegia. An aortic cross clamp was applied and one liter of cardioplegia at 4 degrees Celsius (3 pigs received Celsior and 3 pigs received 500 cc 15 mmol KCl Lazarus/500 cc 7 mmol KCl Lazarus) was given through the aortic cardioplegia cannula. The cardioplegia solutions were vented through the IVC and left superior pulmonary vein. After a liter of solution was given at 150 mmHg, the heart was quickly harvested and biopsies of anterior and posterior wall of the LV were taken and sent to the microscopy lab for evaluation.

In experimental group 3 (NBHD—1 hour death Lazarus), no heparin was given before the aortic cannula was placed and the pig was exsanguinated through the cannula to simulate a trauma death. The heart was then allowed to arrest and it was harvested one hour later. Each heart was then immersed in either Celsior (3 pigs) or Lazarus (6 pigs—3 from beating heart model and 3 from NBHD model) at 4 degrees Celsius for four hours. Myocardial pH and temperature were continuously monitored during storage and biopsies of the anterior and posterior wall were taken at intervals of one hour until four hours post harvest. Also, at the four hour post harvest time point, a two centimeter segment of the left anterior descending artery was then dissected out and sent to the microscopy lab for biochemical evaluation.

In the NBHD model, the hearts were stored for an additional 10 days in Lazarus solution then biopsied again. Livers were also harvested from the NBHD group, stored for 10 days then biopsied.

TABLE 1

Timetable for Biopsies and pH Measurement

| Time Point | Anterior and Posterior LV Wall Biopsies | Myocardial pH Measurement (also recorded at 10 min intervals) | Left Anterior Descending biopsy |
|---|---|---|---|
| Immediately after harvest | Yes | Yes | No |
| 60 minutes post harvest | Yes | Yes | No |
| 120 minutes post harvest | Yes | Yes | No |
| 180 minutes post harvest | Yes | Yes | No |
| 240 minutes post harvest | Yes | Yes | Yes |

Live/Dead Assay

Microscopic and biochemical analyses were performed as follows. The structural viability of the myocardium and endothelium from each biopsy was assessed using the live/dead assay (Molecular Probes, Eugene, Oreg.). Cardiac biopsies were labeled with calcein-AM (green) and ethidium homodimer (red), and images were viewed using multiphoton microscopy. The myocardium and coronary samples are loaded with membrane-permeable calcein-AM ester and membrane impermeable ethidium homodimer. The calcein accumulates in cells and is transformed by the cellular esterases to produce a green fluorescence in living cells ('Live' part of the assay). This was quantified using Metamorph Software to calculate average intensity of fluorescent signal. The membrane-impermeable ethidium homodimer dye enters compromised cells and intercalates with nucleic acids to produce a red fluorescence ('Dead' part of the assay). These cells were counted and recorded as a ratio of the total number of cells.

Determination of Intracellular NO Concentration

The generation of vascular endothelial NO was determined using diaminofluorescein (DAF), as described in previous studies (Thatte H et al., 1999 *Proc. Natl. Acad. Sci.* 96(22): 12583; Nakatsubo N et al., 1998 *FEBS Lett* 427(2):263). The tissue was loaded with membrane permeable 4,5-diaminofluorescein, which is cleaved by endothelial esterases to a membrane impermeable form. This dye is then capable of reacting with intracellularly generated NO to yield the brightly fluorescent triazolofluorescein derivative. The samples were washed with HBSS and mounted for microscopy. Baseline NO production was evaluated then the coronary endothelium was stimulated with 10 microM bradykinin. Intracellular NO concentration was used as an index for endothelial health.

JC-1 Assay: Evaluation of Mitochondrial Membrane Potential

Cardiac myocytes were labeled with JC-1 membrane potential dye. Fluorescence was excited at 488 nm and emission was measured at 520 and 585 nm using narrow band pass filters. JC-1 formed j-aggregates (red) when mitochondria maintain their membrane polarization, but dissociated into monomers (green) upon membrane deoplarization leading to leakage of cytochrome C and proapoptotic factors.

Images from above assays were evaluated in real time using multi-photon microscopy. Standard Western Blots and immunofluorescence were used to determine the structural integrity of the contractile mechanism of the heart and confirmatory assays were performed using multi-photon microscopy.

Multi-Photon and Confocal Microscopy

Multi-photon and Confocal microscopy was carried out as follows. BioRad MRC 1024ES multi-photon imaging system coupled with a mode-locked Spectra-Physics tunable MaiTai titanium-sapphire laser system (pulse duration <80 fs, repetition rate 82 MHz) and a Zeiss Axiovert S100 inverted microscope equipped with a high quality 25X/1.2 NA air, water immersion 40X/1.2 NA 63X/1.2NA and 100X/1.4NA oil immersion objective was used for quantitative and imaging studies in both the fluorescence and transmitted light mode. The major advantages of multi-photon imaging include reduced photobleaching of fluorophores, reduced background fluorescence, reduced photo-damage to living cells, and increased ability to image much deeper (~1000µ depth) into a specimen than is possible with the conventional Confocal microscopy (50µ depth). The technology permits procurement of simultaneous bright field images as well as visualization and quantification of morphological changes. These unique features of multi-photon technology provides the system with versatility, permitting imaging of living or fixed cultured EC as well as intact tissues such as human heart tissues and vessels with a wide variety of fluorescent probes to investigate the various physiological processes. The Bio-Rad MRC 1024ES system is equipped with a conventional krypton-argon laser with 488, 568 and 647 nm emission lines and a femtosecond titanium-sapphire laser, tunable between 735-990 nm. By simultaneously using the conventional and titanium-sapphire lasers, one can ratiometrically image mitochondrial membrane potential, cytosolic free $Ca^{2+}$ (by using, e.g., Calcium orange dye) and simultaneously observe generated NO (using DAF-2 DA) and change in diameter and volume of the whole vein. The esterase activity was measured and standardized at wave-length of 488/568, PMT 1 at 2/864 and PMT2 at 2/1297, laser power, 90% attenuated and Kalman 3 filter (algorithm). The fluorescence was quantitated using MetaMorph image processing software (Universal Imaging, PA).

Example 2

Figure 2:
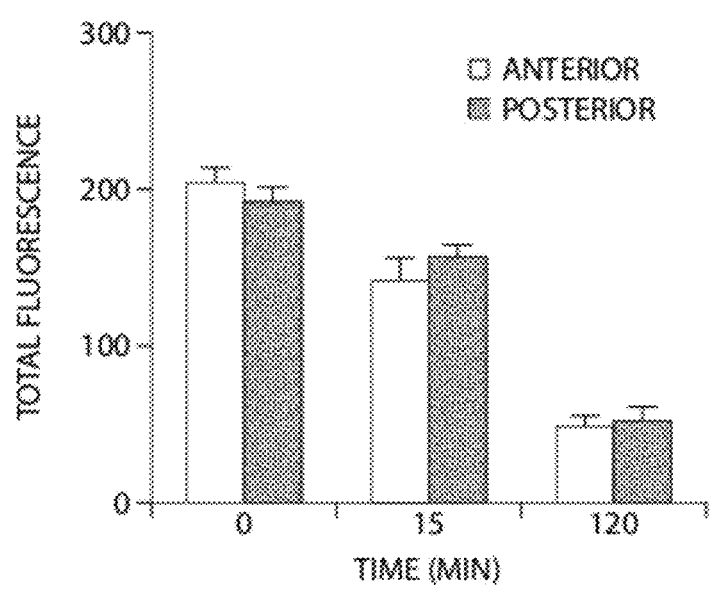
FIG. 2 is a bar chart demonstrating the esterase activity of ventricular cardiomyocytes in the anterior and posterior LV wall at 0 minutes, 15 minutes and 120 minutes post-harvest.
Figure 3:
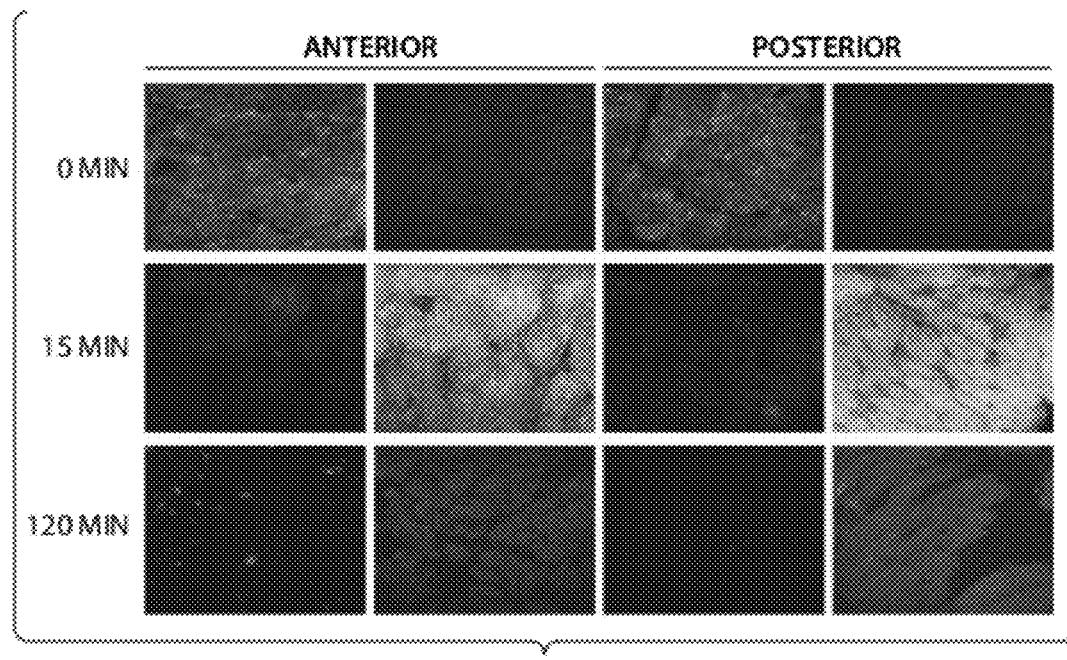
FIG. 3 is a series of photomicrographs showing the ratio of polarized (red) to depolarized (green) ventricular cardiac myocyte mitochondria in the anterior and posterior LV wall at 0 minutes, 15 minutes and 120 minutes post-harvest.
Figure 4:
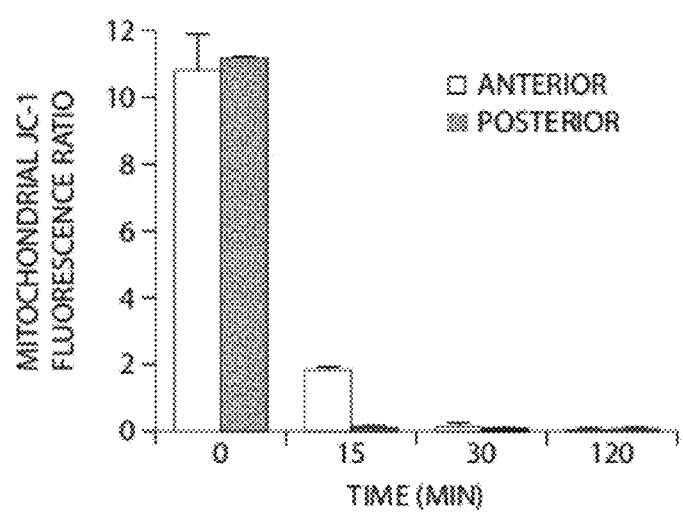
FIG. 4 is a bar graph representing the ratio of polarized to depolarized ventricular cardiac myocyte mitochondria in the anterior and posterior LV wall at 0 minutes, 15 minutes, 30 minutes, and 120 minutes post-harvest.

Evaluation of the Effects of Lazarus Solution on Tissues and Organs Control Group The results of the live/dead assay on the control group (cardiac decay) are shown in FIGS. 1 and 2. There was a time-dependant decrease in esterase activity (green fluorescence) and a time-dependant increase in cell death/necrosis (red fluorescence) in ventricular cardiomyocytes in both the anterior and posterior left ventricular (LV) wall in the control group over 120 minutes (FIGS. 1 and 2). FIG. 2 depicts a graphical representation of the decrease in esterase activity over time in the control group (cardiac decay). Moreover, the results of the JC-1 assay to evaluate mitochondrial membrane potential in the control group indicated that there was a time-dependant depolarization of the ventricular cardiac myocyte mitochondrial membrane (FIG. 3: left column in each group represents polarization (red); right column in each group represents depolarization (green)). As shown in the graphical representation in FIG. 4, the mitochondria in the control group become increasingly depolarized.

Experimental Groups

The objective of the following experiments was to compare the Lazarus solution of the invention to Celsior solution, a commonly used storage solution in cardiac transplantation. As described above, and illustrated in FIG. 28, each porcine heart was preserved in the indicated storage solution (Celsior or Lazarus) for 4 hours. The Celsior group exhibited less esterase activity (FIGS. 5, 6, and 7), greater necrosis (FIG. 5), and greater mitochondrial membrane depolarization (FIG. 8) (live/dead assay and JC-1 assay, respectively) than the Lazarus beating heart model and Lazarus 1 hour death (NBH) groups.

Figure 5:
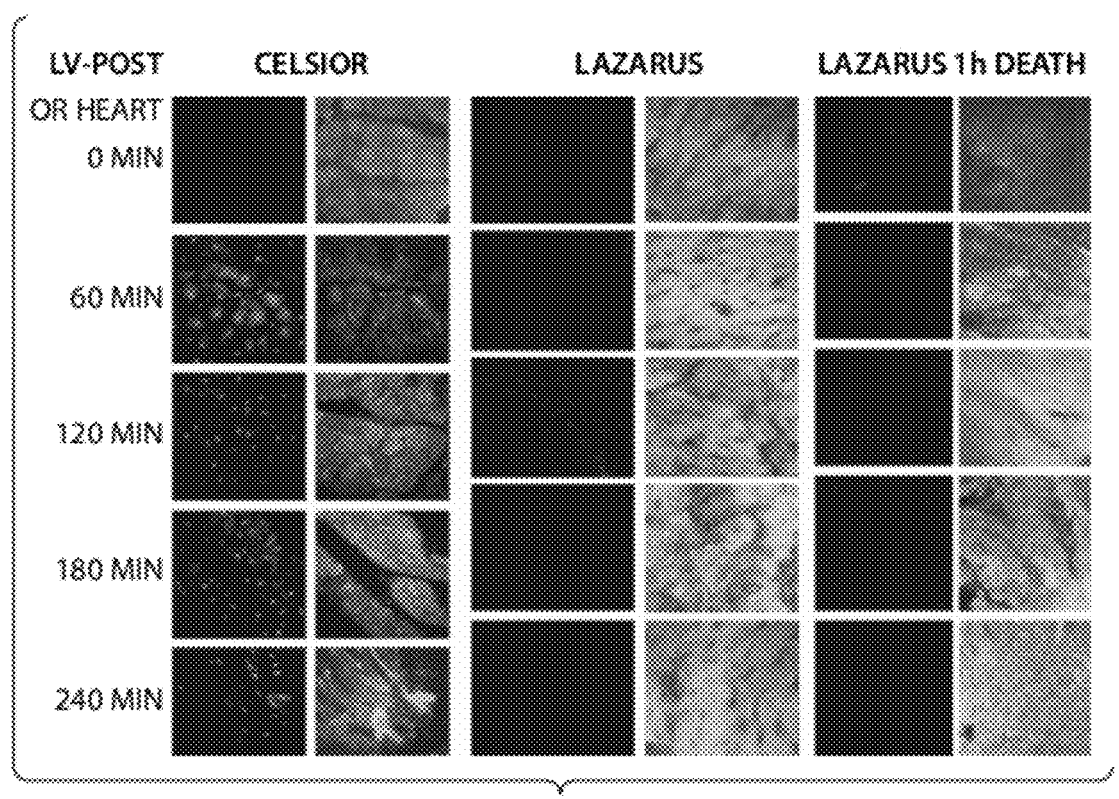
FIG. 5 is a series of photomicrographs indicating the necrosis (red) and esterase activity (green) of the posterior LV wall of porcine hearts that were incubated in either the solution of the invention, referred to as "Lazarus", or Celsior for 4 hours.
Figure 6:
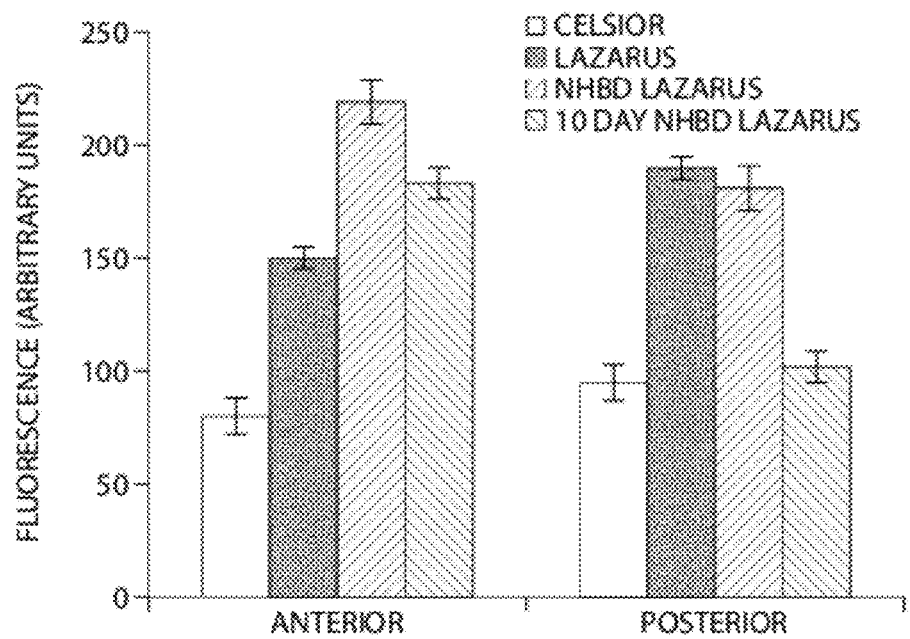
FIG. 6 is a graphical representation of the esterase activity in the anterior and posterior LV myocardium in each experimental group, i.e., 4 hour storage in Celsior; 4 hour storage in Lazarus; NBHD 4 hour storage in Lazarus; and NBHD 10 day storage in Lazarus.
Figure 7:
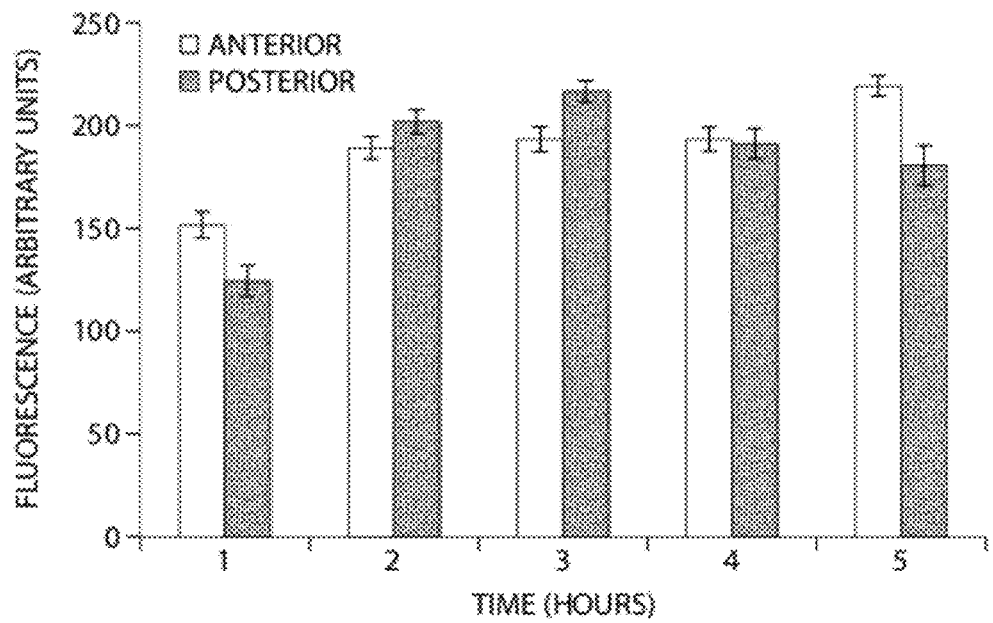
FIG. 7 is a bar graph identifying the esterase activity in the anterior and posterior LV wall of the NBHD model after 1 hour, 2 hours, 3 hours, 4 hours, and 5 hours of storage in Lazarus solution.

As shown in FIG. 5, while the Celsior group exhibited increasing necrosis (red; left column in each group) and decreasing esterase activity (green; right column in each group), both Lazarus groups exhibited minimal necrosis (red) and increasing esterase activity (green). The ability of Lazarus to preserve porcine non-beating hearts for 10 days without changing solution was also evaluated (FIG. 6). The results in FIG. 6 graphically illustrating the esterase activity in each experimental group indicate that there were more living cells in each Lazarus group as compared to the Celsior group, suggesting that Lazarus was more effective at preserving the porcine hearts. Next, the esterase activity of 1 hour cadaveric hearts stored in Lazarus solution for 4 hours at 10° C. was determined. As shown in FIG. 7, there was an increase in esterase activity from baseline and stabilization thereafter in the NBHD model stored in Lazarus for 4 hours.

Figure 8:
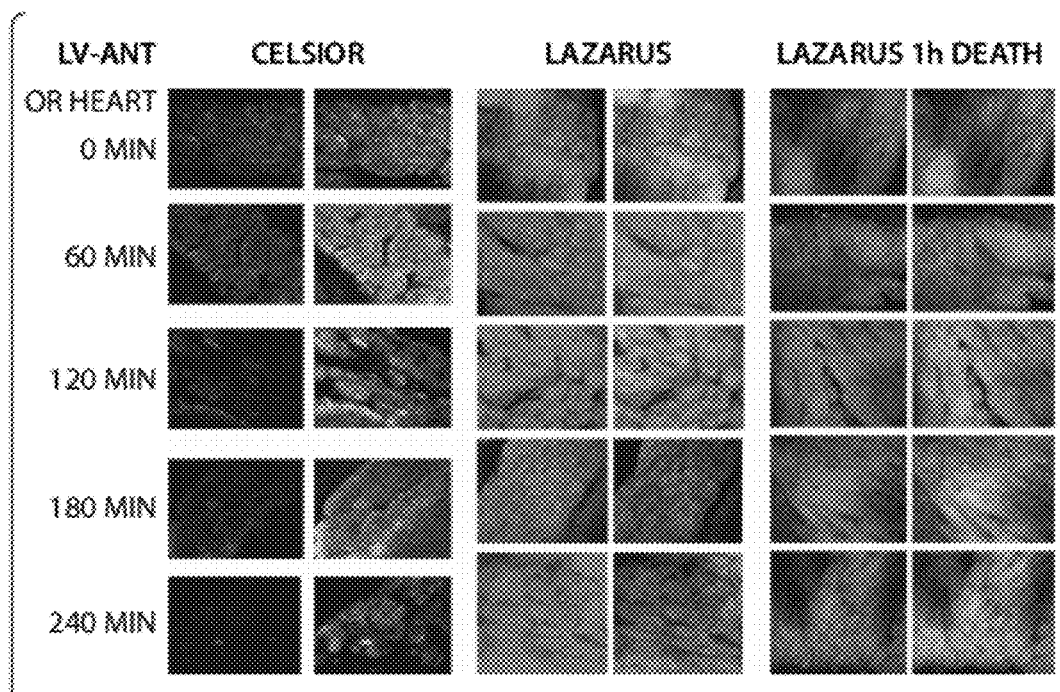
FIG. 8 is a series of images demonstrating the ratio of red (polarized) to green (depolarized) cardiac myocyte mitochondria in the anterior LV wall after 0 minutes, 60 minutes, 120 minutes, 180 minutes, and 240 minutes of storage in either Celsior or Lazarus solution.

Mitochondrial membrane potential supplies the energy by which ATP is generated in the Krebs Cycle. As such, mitochondrial membrane potential in the porcine heart preserved in storage solution for 4 hours was determined via the JC-1 assay described above. A ratio of red (polarized; left column in each group) to green (depolarized; right column in each group) greater than 1 represents healthy mitochondria within myocytes, i.e., ready to produce ATP. As shown in FIG. 8, the mitochondrial membrane potential of porcine hearts was maintained better in each of the Lazarus groups than it was in the Celsior group. Moreover, as shown in FIG. 8, mitochondrial membrane polarization was restored in the Lazarus groups over the course of 240 minutes.

Figure 9:
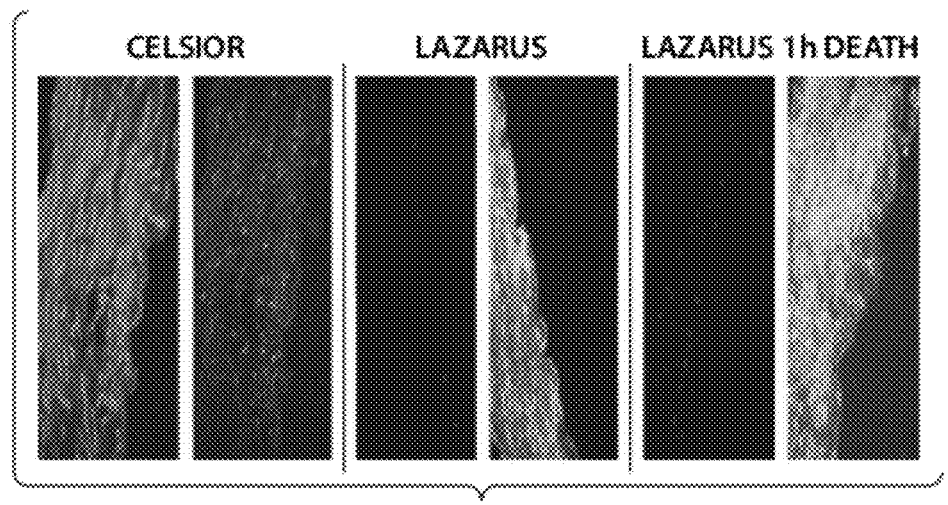
FIG. 9 is a series of photomicrographs showing necrosis (red) and esterase activity (green) of porcine heart left anterior descending artery that was incubated in either Lazarus or Celsior for 4 hours.

The live/dead assay was also performed on the porcine heart left anterior descending artery (LAD) preserved in solution for 4 hours. As shown in FIG. 9, there was significant necrosis (red; left column in each group) of the coronary artery in the Celsior group and minimum necrosis in both Lazarus groups. Esterase activity (green; right column in each group) was also more robust in each Lazarus group as compared to the Celsior group.

Figure 10:
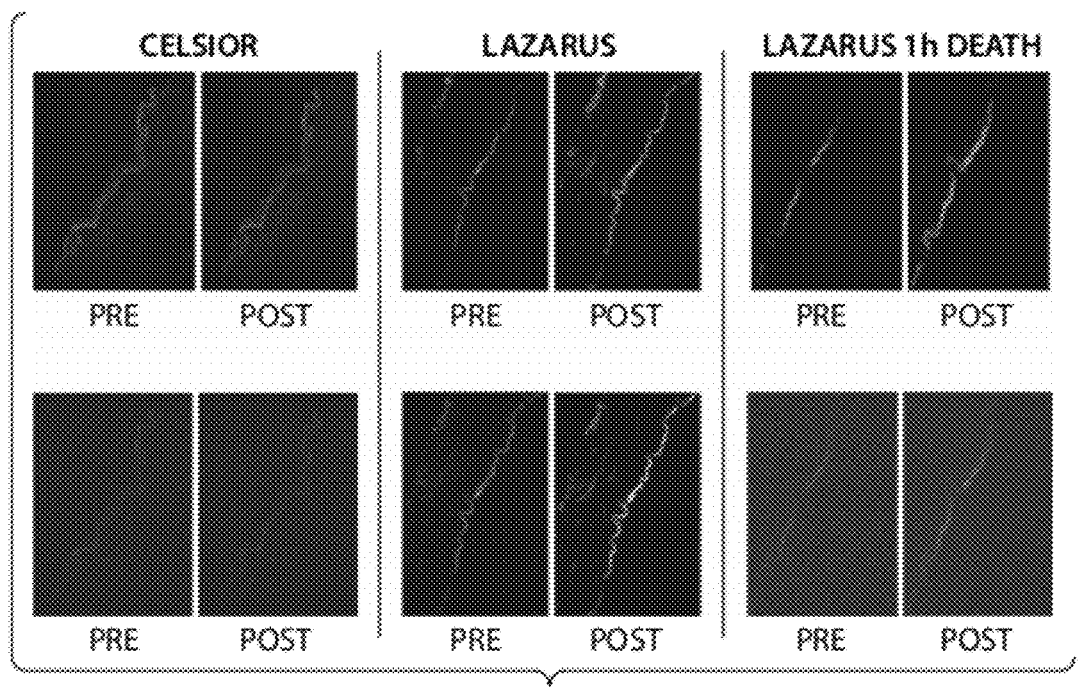
FIG. 10 is a series of images depicting calcium mobilization (red) and NO production (green) of Celsior or Lazarus-treated porcine heart left anterior descending artery before and after stimulation with bradykinin.
Figure 11:
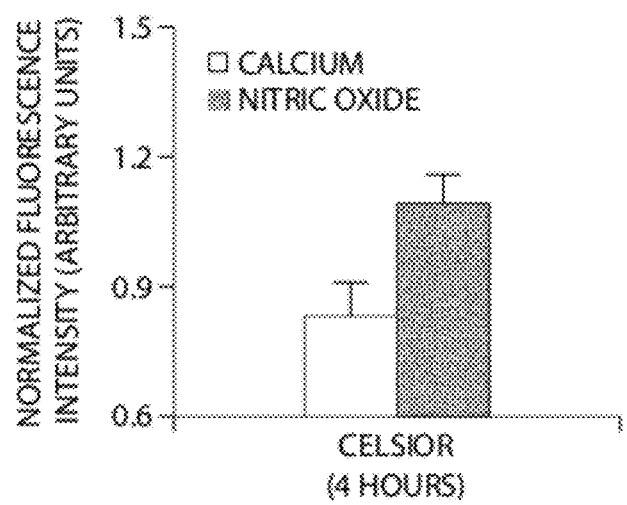
FIG. 11 is a graphical representation of calcium mobilization and NO production of Celsior-treated porcine heart left anterior descending artery after stimulation with bradykinin.
Figure 12:
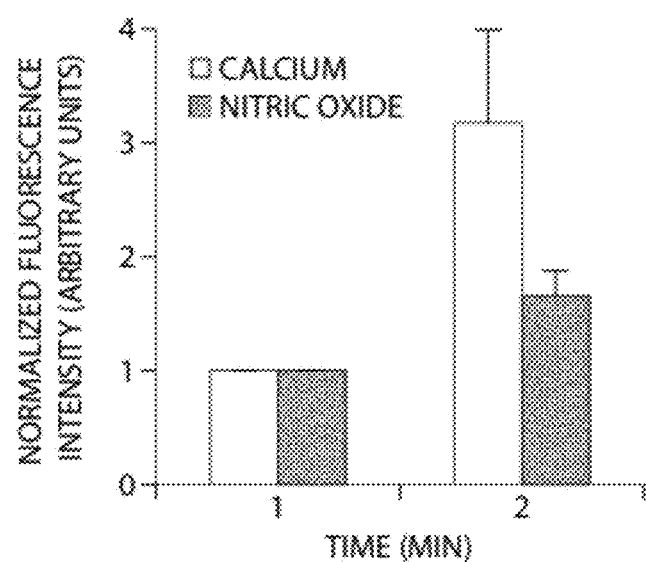
FIG. 12 is a bar graph demonstrating calcium mobilization and NO production of 4 hour Lazarus-treated porcine heart (1 hour post-mortem) left anterior descending artery after stimulation with bradykinin.

Endothelial function (calcium mobilization and nitric oxide (NO) production) was evaluated before and after stimulation with bradykinin in porcine heart LAD preserved in solution for 4 hours. There was a better preservation of endothelial function in both Lazarus groups, as indicated by increased calcium mobilization and nitric oxide production in response to Bradykinin (FIGS. 10, 11, 12). As shown in FIG. 10, both Lazarus groups had greater calcium mobilization (red; top row in each group) and NO production (green; bottom row in each group) at baseline and after bradykinin stimulation (pre and post, respectively). FIG. 11 is a graphical representation of endothelial response (calcium mobilization and NO generation) to bradykinin in LAD of porcine hearts preserved in Celsior. Both are less than 1.2 from baseline. FIG. 12 is a graphical representation of endothelial response (calcium mobilization and NO generation) to bradykinin in LAD of NBHD porcine hearts (1 hour death) preserved in Lazarus for 4 hours. The response to simulation was more robust (>2) than in the Celsior beating heart model group shown in FIG. 11. These results demonstrate that storage in Lazarus solution preserved endothelial function better than storage in Celsior.

Structural Assays Using Western Blots and Immunoblots

Figure 13:
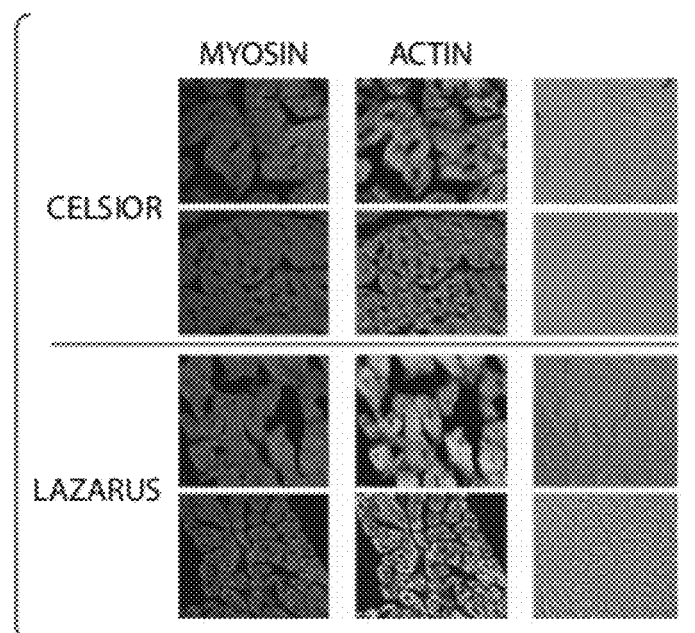
FIG. 13 is a series of images depicting immunofluorescence labeling of Myosin and Actin in the myocardium after 4 hours incubation in either Celsior or Lazarus.
Figure 14:
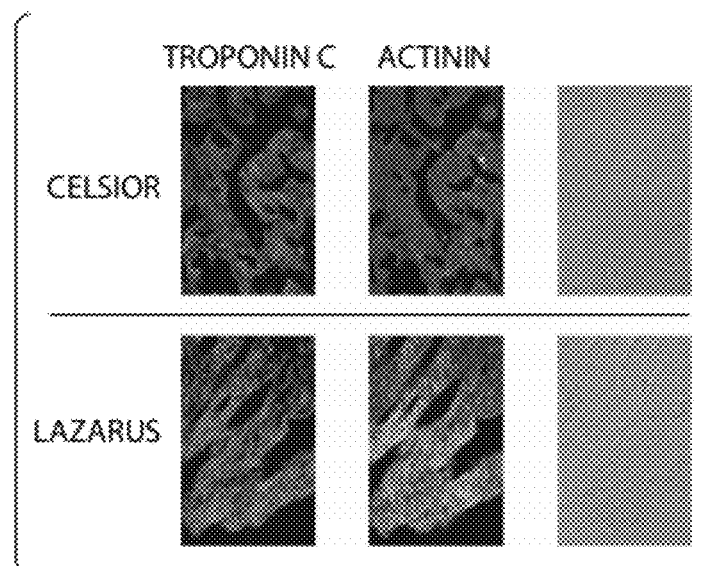
FIG. 14 is a series of photomicrographs demonstrating immunofluorescence labeling of Troponin C and Actinin in the myocardium after 4 hours of incubation in Celsior or Lazarus.

The structural integrity of the contractile apparatus in the heart was evaluated by labeling structural components of the myocardium. Structural components of the myocardium were preserved (FIGS. 13, 14, 15, and 16) after storage in Lazarus for four hours. FIG. 13 shows the results of immunofluorescence labeling of Myosin and Actin after 4 hours of storage in Celsior or Lazarus. FIG. 14 shows the results of immunofluorescence labeling of Troponin C and Actinin after 4 hours in Celsior or Lazarus. As shown in FIG. 14, Troponin C and Actinin (structural components of the contractile mechanism) are preserved in Lazarus. Moreover, the results show a striated appearance to the fluorescence in the Lazarus group (not the Celsior group), suggesting organization of these structural proteins into an intact contractile apparatus.

Figure 15:
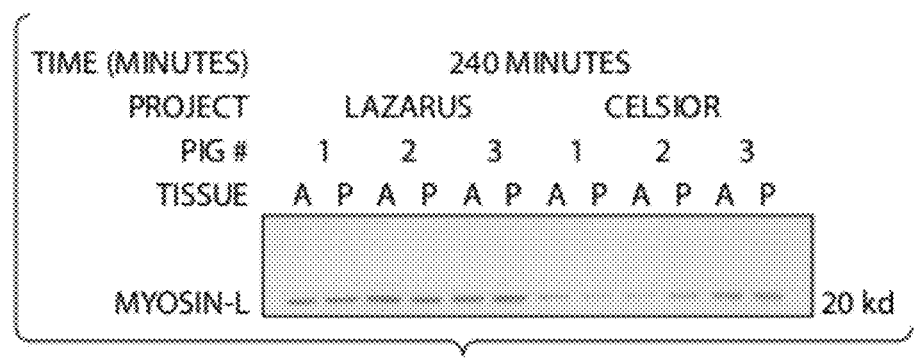
FIG. 15 is a photograph of a Western blot showing the presence of Myosin light chain protein in anterior (A) and posterior (P) biopsies of porcine post-mortem heart stored in Lazarus or Celsior for 240 minutes.
Figure 16:
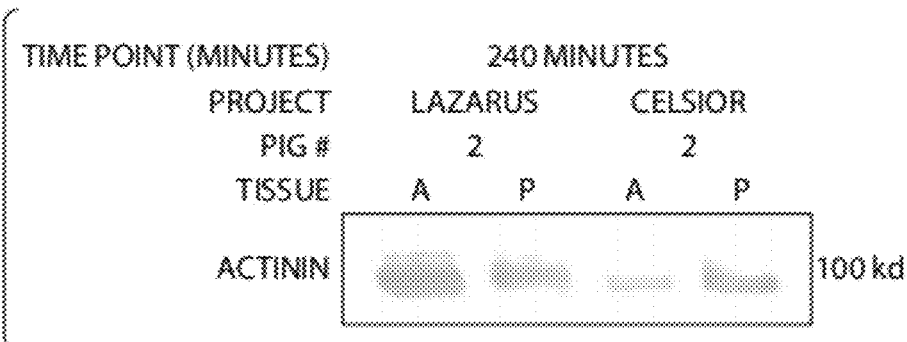
FIG. 16 is a photograph of a Western blot showing the presence of Actinin in anterior (A) and posterior (P) biopsies of porcine post-mortem heart stored in Lazarus or Celsior for 240 minutes.

As shown in FIG. 15, Western blot analysis was performed for anterior (A) and posterior (P) biopsies of pig #1, 2, and 3 post mortem heart stored in Lazarus or Celsior. Myosin light chain protein (20 kd) was identified using mouse anti-Myosin (light chain; cat#M4401 from Sigma; 10% PAGE; 7.5 ug/well loading). As shown in FIG. 16, Western blot analysis was performed for anterior (A) and posterior (P) biopsies of pig #2 post mortem heart stored in Lazarus or Celsior. Actinin protein (100 kd) was identified using mouse anti-actinin (cat#7811 from Sigma; 10% PAGE; 15 ug/well loading). These Western blots illustrate the superior preservation of the two structural components of the myocyte contractile mechanism (Myosin light chain and Actinin), as represented by wider bands on the blot after storage in Lazarus as compared to Celsior.

Figure 17:
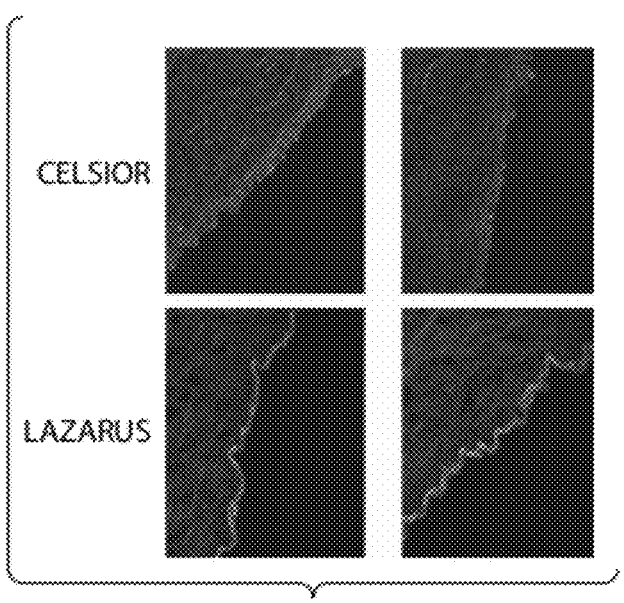
FIG. 17 is a series of photomicrographs showing immunofluorescence labeling of eNOS in the endothelium after 4 hours of incubation in Celsior or Lazarus.

In order to confirm that endothelial function was preserved better in Lazarus than in Celsior, immunofluorescence labeling of eNOS in LAD after 4 hours storage in Celsior or Lazarus was performed. eNOS is the enzyme responsible for NO production in the endothelium. As shown in FIG. 17, the eNOS staining in the endothelium of the Lazarus-stored heart was more robust than that in the Celsior-stored heart. These results indicate that Lazarus is more effective at preserving endothelial cells than Celsior.

10 Day Data from the Heart and Liver

Figure 18:
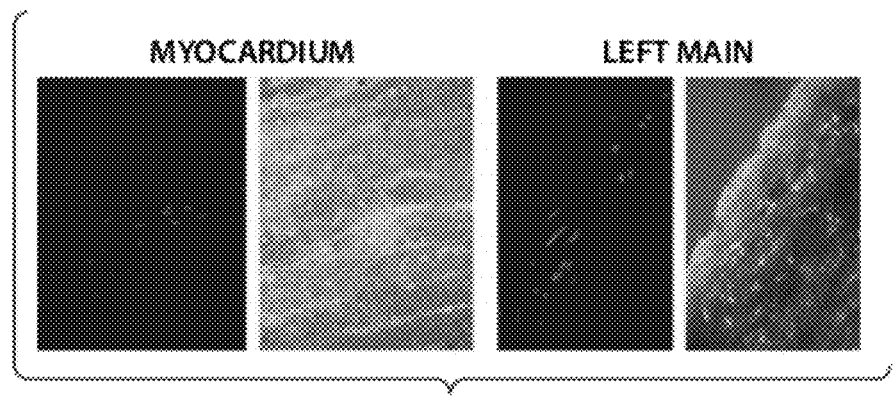
FIG. 18 is a series of images depicting necrosis (red) and esterase activity (green) in the myocardium and left main coronary artery (1 hour post-mortem) after 10 days of storage in Lazarus solution.
Figure 19:
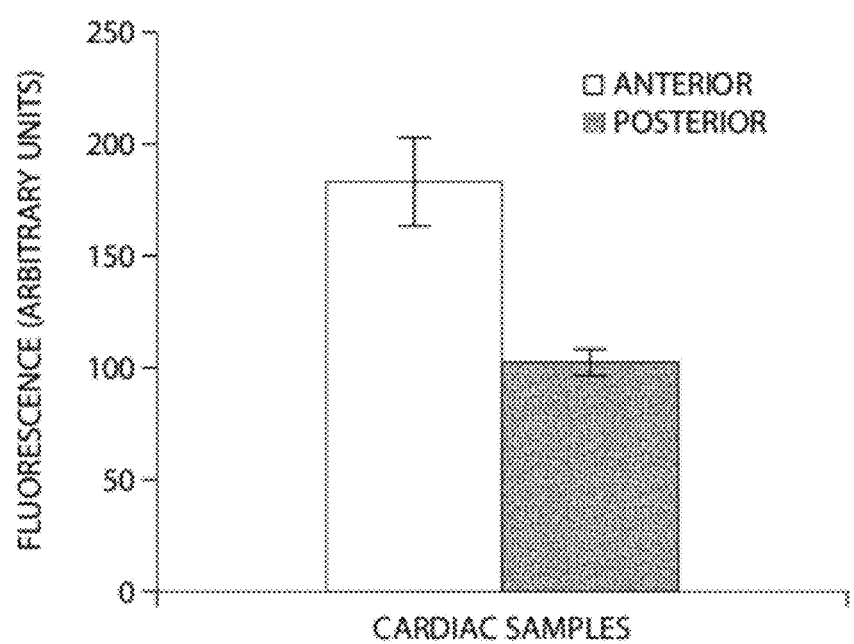
FIG. 19 is a bar chart demonstrating esterase activity in the anterior and posterior myocardium (1 hour post-mortem) after 10 days of storage in Lazarus solution.
Figure 20:
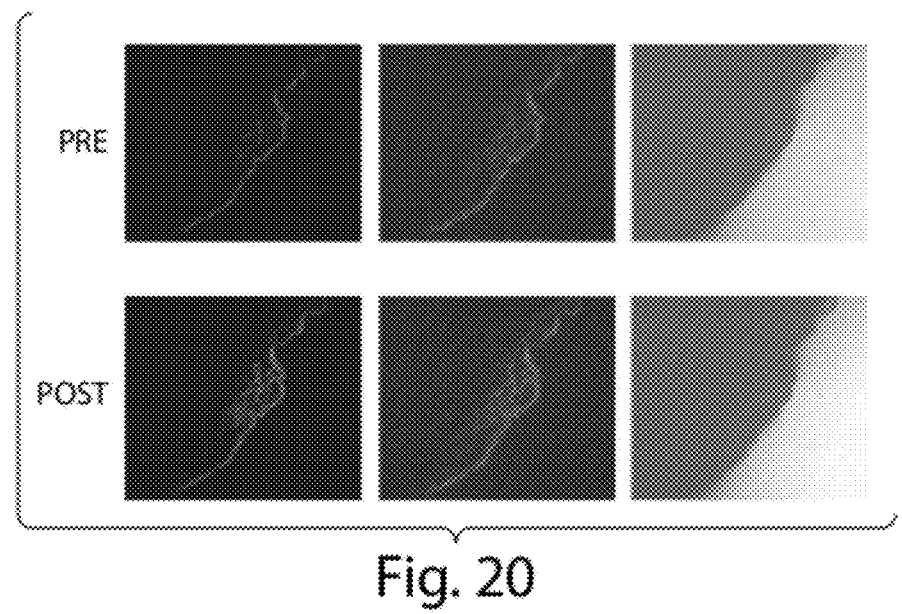
FIG. 20 is a series of photomicrographs showing calcium mobilization (red) and NO production (green) of 10 day Lazarus-treated porcine heart left anterior descending artery after stimulation with bradykinin.
Figure 21:
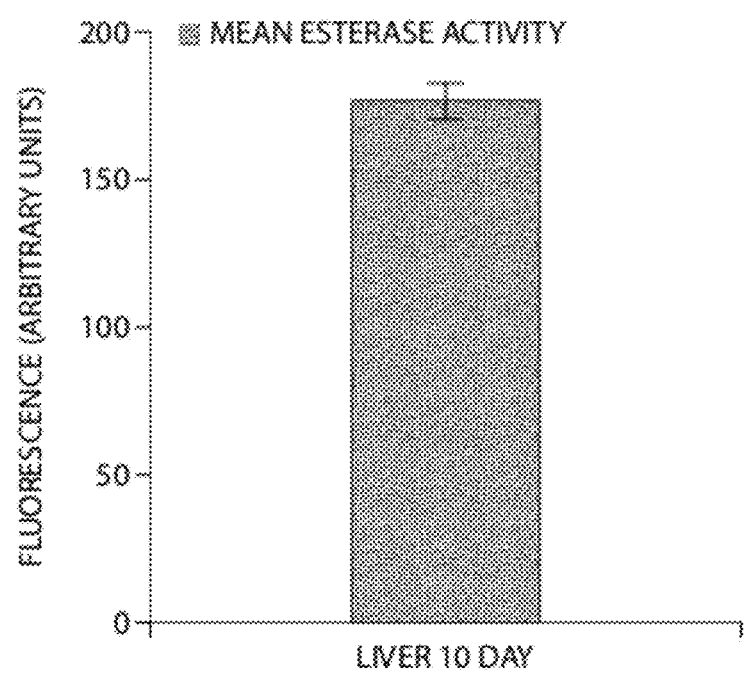
FIG. 21 is a graphical representation of the esterase activity in a liver after 10 days of storage in Lazarus solution.

In additional studies, Lazarus was evaluated as a storage solution for 10 days in the heart and liver. After 10 days, there was minimal necrosis, robust esterase activity (live/dead assay—FIGS. 18 and 19), and preserved endothelial function in the heart stored in Lazarus (FIG. 20). Moreover, there was also minimal necrosis and robust esterase activity in the Lazarus-stored liver (FIGS. 20 and 21). The live/dead assay was performed on the myocardium and left main coronary artery of the 1 hour cadaveric group stored in Lazarus for 10 days. As shown in FIG. 18, there was minimal necrosis (red; left column in both groups) and significant esterase activity (green; right column in both groups) in the myocardium and left main coronary artery (1 hour post-mortem) after 10 days in Lazarus solution, suggesting that storage in Lazarus solution for 10 days preserved the heart. FIG. 19 is a graphical representation of the preservation of esterase activity in the myocardium stored in Lazarus for 10 days. The ability of Lazarus to preserve esterase activity after 10 days in solution was greater than the ability of Celsior to preserve esterase activity after 4 hours in storage. (See FIG. 6 for a direct comparison.)

Endothelial function (calcium mobilization and NO production) was evaluated in LAD stimulated with bradykinin after 10 days storage in Lazarus. As shown in FIG. 20, Lazarus solution preserved calcium mobilization (red; left column) and NO production (green; middle column) in LAD, suggesting that endothelial function was preserved after 10 days storage in Lazarus.

Figure 22:
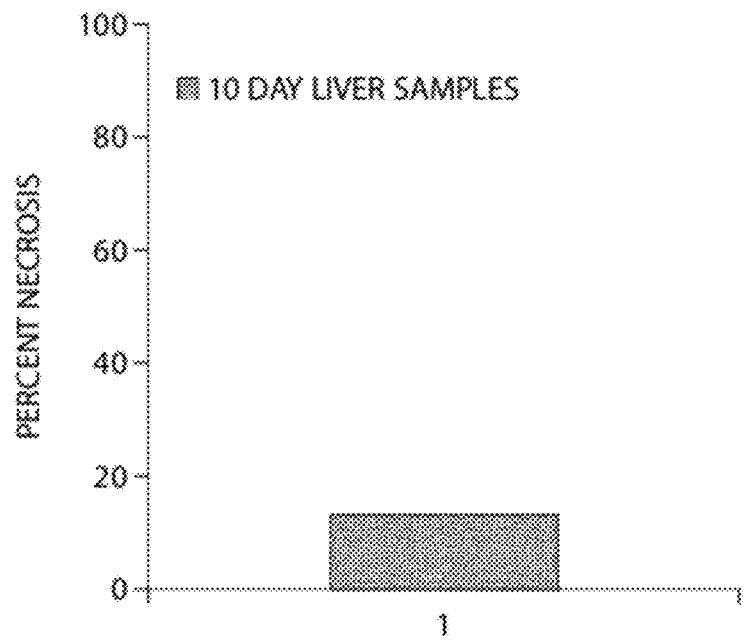
FIG. 22 is a bar graph showing the percent necrosis in a liver after 10 days of storage in Lazarus solution.

FIG. 21 is a graphical representation showing that esterase activity was preserved in the liver stored in Lazarus for 10 days at 4° C. FIG. 22 shows that the average percent necrosis in liver samples stored in Lazarus solution for 10 days at 4° C. was less than 15%, suggesting that 10 days of storage in Lazarus solution preserves the liver.

Example 3

Perfusion Devices

Figure 26:
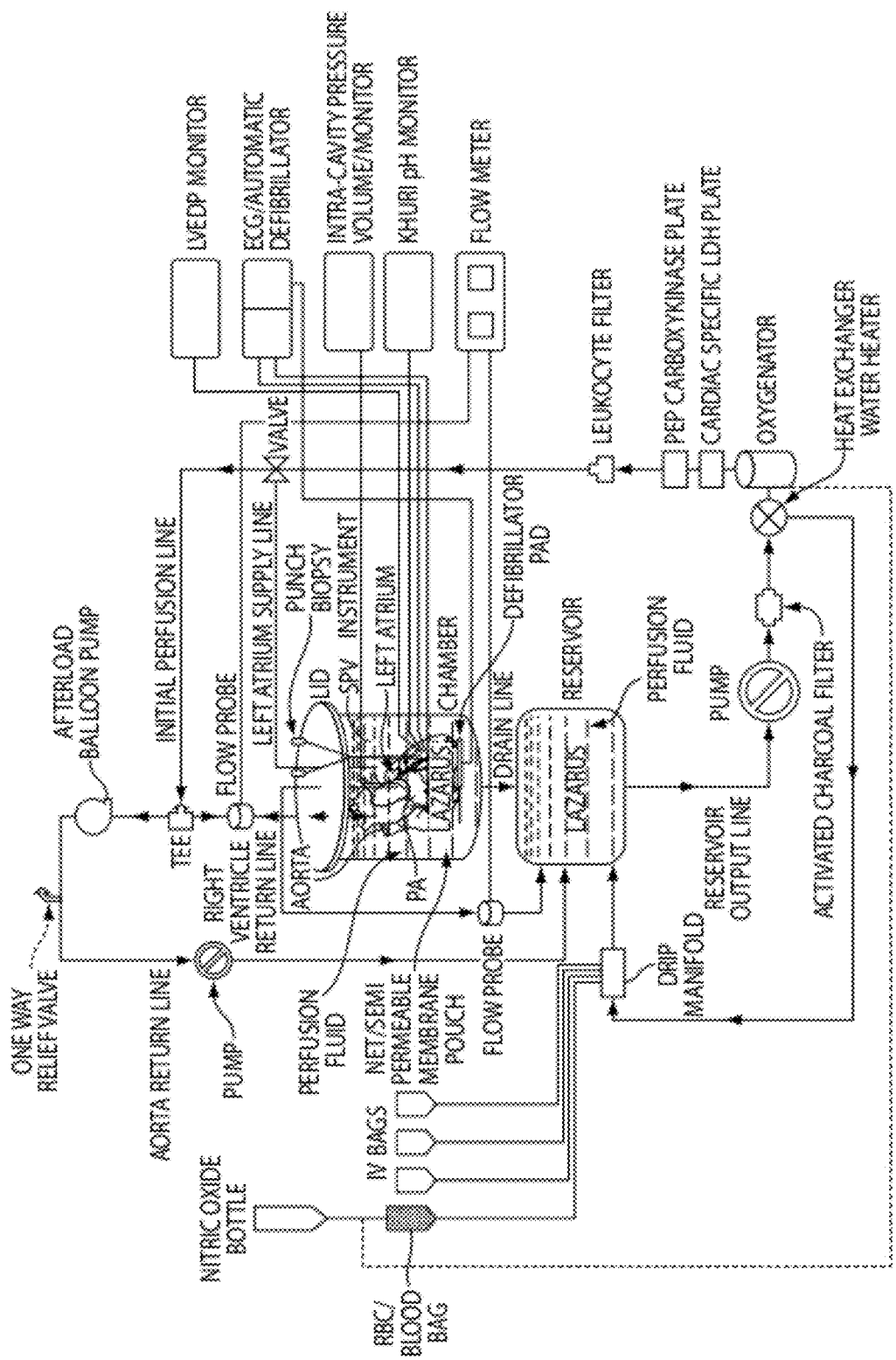
FIG. 26 is a line drawing of an ex vivo resuscitation and preservation device for a heart.
Figure 27:
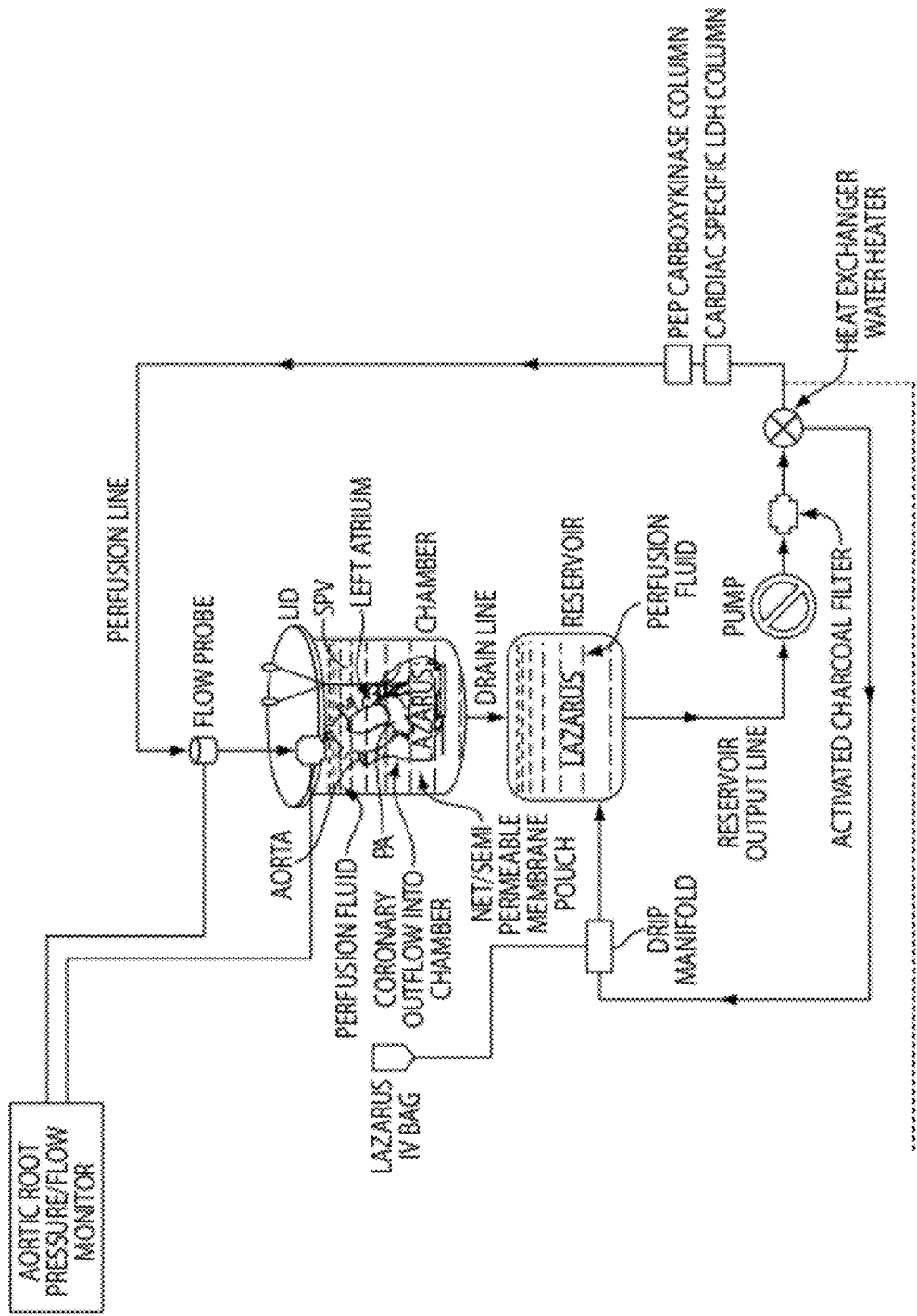
FIG. 27 is a line drawing of an ex vivo preservation device of a heart in non-working state.

FIGS. 26 and 27 depict perfusion devices and systems. FIG. 26 shows a system for ex vivo resuscitation and preservation of a human heart. The afterload balloon pump controls afterload blood pressure in the aorta. The afterload balloon pump is optionally replaced with a pressure regulator or valve. Cardiac parameters are maintained within the following ranges: afterload and/or balloon pump pressure is 60-80 mm Hg; aortic root pressure is 40-80 mm Hg (for perfusion during storage); flow rate is 100-300 cc/min.; cardiac output (CO) is >2 L/min.; and blood pressure (BP) 120-140/60-80 mm Hg. The chamber and reservoir contain the solution, e.g., Lazarus solution. Two elements of the system render it self-sustaining: phosphoenolpyruvate (PEP) caryboxykinase plate and a cardiac specific lactate dehydrogenase (LDH) plate.

A method for resuscitating (waking up) a heart is carried out as follows:
1. Rapid harvest and arrest of the heart with high potassium (15 mM) in very cold Lazarus (4° C.).
2. Rapid instrumentation of the heart, maintaining low temperature—i.e. minimum residence time at the room temperature.
3. Transfer to excess cold Lazarus and storage for 24 hours at 4° C.

Next Day:
1. Well-established blood chemistry, as required.
2. Keep ready-cold Lazarus cardioplegia with sodium bicarbonate 19 mEq, KCl 18.5 mEq, MgSO4, 37 mEq/L.
3. Keep ready non-oxygenated blood.
4. Mix blood and Lazarus 4:1 (assured proper chemistry; i.e. confirm final concentrations of calcium, magnesium, potassium and sodium)
5. Prime the perfusion system with #4—maintain temperature at 15-20° C. or colder
6. Rapidly hook up the heart into the apparatus; after physical examination (color, texture, palpability, edema/shrinkage etc).
7. Perfuse the heart via the aortic root: @ with non-oxygenated blood (10-15% Hct.) cardioplegia (Lazarus containing, sodium bicarbonate 19 mEq, KCl 18.5 mEq, MgSO4, 37 mEq/L) 4:1, at 40 mm Hg for 20-30 min, maintained at 15° C.
8. Reperfuse with oxygenated blood (>15% Hct) at 20° C. with perfusion pressure of 40 mmHg for 20 min. Elevate the perfusion pressure to 60 mmHg and the temperature is increased stepwise to 37° C. over 30 min. The organ is slowly warmed to, e.g., 10, 18, 20, 22, and so on until the organ reaches 37° C.
9. Through the course of the experiment check for hyper contracture.
10. The heart goes into sinus rhythm with normal CO and LVEDP, systolic/diastolic pressure.
11. Switch over to perfusing the heart via normal physiological rout, through the pulmonary vein or left atrium (heart in working state).
12. Maintain the heart in beating state, until desired steady-state is achieved.
13. Measure cardiac function parameters.

A solution of the invention, referred to below as beta-Lazarus solution, was used to restart the heart after storage in alpha-Lazarus. Table 2 displays the concentrations of each reagent in beta-Lazarus. The pH is adjusted to 7.4 using sodium bicarbonate (8.4%) or THAM, and maintained at 21-37° C.

Alternative Protocol:
1. Hook up the heart to the perfusion system.
2. Circulate Beta-lazarus through the heart in non-working state configuration (i.e. through the aortic root) at 40-120 mm Hg, until the perfusate and/or heart pH stabilizes at >7.2; this process can take 30 or more min of perfusion to achieve this state.
3. For this to happen, the pH of the circulating beta-Lazarus needs to be adjusted often as required, with sodium bicarbonate or THAM, based on-line CDI and blood gas monitoring. Once the steady-state is reached, maintain the pH of the circulating beta-Lazarus at 7.4.
4. Adjust the beta-Lazarus, calcium, potassium and sodium concentration to physiological levels as required, based on on-line monitoring.
5. Once the pH of the solution remains stable at 7.4 for 5-10 min, slowly drain the beta-Lazarus, while replacing it with platelet and WBC free whole blood till a ration of 4:1 (blood:beta-lazarus) is reached in the reservoir. Alternatively, this ration can be varied to 5:0, 3:2, 2:3, etc. as desired.
6. Once the system regains steady state=physiological levels of electrolytes and pH (on-line measurements), slowly raise the temperature of perfusing blood:lazarus, @ 1° C. every 2-5 min, until 37° C. is reached. Keep adjusting the electrolytes and pH during this period, as required.
7. Once the temperature reaches 28-30° C., the heart should start beating and continue to do so as the temperature is raised to 37° C. At this stage, the blood:Lazarus mixture can be wholly replaced by whole blood.
8. The system is then switched to working state as described and monitored as required.

TABLE 2

Composition of Beta-Lazarus Organ Preservation Solution for Restarting the Heart

| Components | Concentration | |
| --- | --- | --- |
| | mM | gm/L |
| Distilled water | | 1.00 L |
| Calcium chloride | 1.30 | 0.191 |
| Potassium chloride | 4.00 | 0.300 |
| Potassium phosphate (monobasic) | 0.44 | 0.060 |
| Magnesium chloride (hexahydrate) | 0.50 | 0.101 |
| Magnesium sulfate (heptahydrate) | 0.50 | 0.123 |
| Sodium chloride | 130.00 | 7.60 |
| Sodium bicarbonate | 4.20 | 0.35 |
| Sodium phosphate (dibasic; heptahydrate) | 0.19 | 0.05 |
| D-glucose | 10.00 | 1.800 |
| Glutathione (reduced) | 1.50 | 0.461 |
| Ascorbic acid | 1.00 | 0.176 |
| L-arginine | 1.00 | 0.211 |
| L-citrulline malate | 1.00 | 0.175 |
| Creatine monohydrate | 5.00 | 0.746 |
| L-carnitine | 2.50 | 0.500 |
| Insulin (10 mg/ml) | | 0.50 ml/L |

A system for ex vivo preservation of a human heart in a non-working state is shown in FIG. 27. Using this system, an organ such as a heart is maintained for up to 10 days or 2 weeks prior to resuscitation. Perfusion is carried out via the aorta, and a flow, e.g., direct or pulsatile flow, is maintained. The flow of solution inhibits activation of apoptotic genes, and the flow rate is approximately 40 ml/min. The storage unit is kept at a temperature of 4-21° C., e.g., in the range of 4-15° C. To maintain such a temperature, the unit is placed in a refrigerated chamber or cold room. Alternatively, the system includes a heat exchanger to regulate and maintain the desired temperature.

In one aspect, the heart is arrested in the solution of the invention with a high $K^+$ concentration at a cool temperature. Preferably, the high $K^+$ concentration present in the solution does not damage the endothelium and ionic channels of the heart. More preferably, the high $K^+$ concentration is flushed out of the heart to prevent damage. Optionally, the magnesium concentration in the solution of the invention is altered.

In another aspect, the functionality of the beating heart is assessed to determine if the heart is suitable for transplantation. Optionally, the contractility of the heart is assessed and/or the pH of the heart is assessed to determine if the heart is suitable for transplantation. Alternatively, the pressure and/ or volume in the chambers of the heart is determined in order to assess the functionality of the heart.

In one aspect, the system of the invention maintains the tissue at a cool temperature, e.g., in the range of 4-15° C. The pH of the solution is determined at regular intervals, e.g., every 1 hour, every 2 hours, every 4 hours, every 8 hours, or every 10 hours. Fresh solution of the invention is added to the system when the pH drops below 6.8 in order to increase the pH of the solution bathing the tissue. This process is repeated until the pH stabilizes around 6.8 to 7.0, indicating that the ATP stores in the tissue have been replenished. Preferably, the tissue is a heart. In one aspect, the heart is restarted when the pH of the system stabilizes between 6.8 and 7.0.

Alternatively, the pH of the tissue is determined at regular intervals, e.g., every 1 hour, every 2 hours, every 4 hours, every 8 hours, or every 10 hours. Preferably, the tissue is a heart. Optionally, the pH of the heart is determined using pH electrodes. Alternatively, the pH of the heart is determined using a fiber optic probes system. In one aspect, the pH of the myocardium, the anterior wall, and/or the posterior wall of the heart is determined.

The pH of the tissue or solution is determined to assess whether the tissue is suitable for transplantation. Preferably, the tissue is a heart. A pH of the heart between 6.8 and 7.0 indicates that the heart was adequately protected during storage. Preferably, the pH of the heart suitable for transplantation is between 6.8 and 7.0.

The invention also provides that the pH of the tissue or solution is determined during the excision, storage, or resuscitation of the tissue/organ. Preferably, the tissue/organ is a heart.

In yet another aspect, the pressure in the chambers of the heart is determined. Optionally, the ventricular pressure of the heart is determined. In one aspect, the pressure is determined using a Mylar catheter.

In one aspect, the heart is stored in the solution of the invention (static). In another aspect, the coronary artery of the heart is perfused.

In yet another aspect, the device contains inputs and outputs to the heart. Optionally, the left and right pulmonary vessels are cannulated. Preferably, the aortic and left atrial cannula drain into the device.

What is claimed is:

1. A method producing a physiological solution for the preservation or resuscitation of a tissue or organ comprising:
    mixing one or more physiological salts, glucose, glutathione, ascorbic acid, arginine, citrulline, adenosine, carnosine, creatinine and carnitine with water to form an aqueous physiological solution, wherein said one or more physiological salts are selected from the group consisting of calcium chloride, potassium chloride, potassium phosphate, magnesium chloride, magnesium sulfate, sodium chloride and sodium phosphate.

2. The method of claim 1 further comprising adding to the physiological solution one or more compounds selected from the group consisting of dichloroacetate, sodium bicarbonate and insulin.

3. The method of claim 2 further comprising adjusting a pH of the physiological solution to 7.4.

4. The method of claim 2 comprising adding sodium bicarbonate to the solution to bring the solution to a pH of 7.4.

5. The method of claim 1 further comprising mixing the water with calcium chloride, potassium chloride, potassium phosphate, magnesium chloride, magnesium sulfate, sodium chloride and sodium phosphate.

6. A method for preparing a physiological solution for preserving or resuscitating a tissue or organ comprising:
    mixing water with calcium chloride, potassium chloride, potassium phosphate, magnesium chloride, magnesium sulfate, sodium chloride, sodium phosphate, glucose, glutathione, ascorbic acid, arginine, citrulline, adenosine, carnosine, creatinine and carnitine to form an aqueous physiological solution.

7. The method of claim 6 further comprising adding to the physiological solution one or more compounds selected from the group consisting of dichloroacetate, sodium bicarbonate and insulin.

8. The method of claim 7 further comprising adjusting a pH of the physiological solution to 7.4.

9. The method of claim 7 comprising adding sodium bicarbonate to the solution to bring the solution to a pH of 7.4.

* * * * *